(12) United States Patent
Marin

(10) Patent No.: US 9,918,984 B2
(45) Date of Patent: Mar. 20, 2018

(54) METHODS AND COMPOSITIONS FOR TREATING DIABETES, METABOLIC SYNDROME AND OTHER CONDITIONS

(71) Applicant: CORTENDO AB (PUBL), Trevose, PA (US)

(72) Inventor: Per Marin, Vastra Frolunda (SE)

(73) Assignee: CORTENDO AB (PUBL), Trevose, PA (US)

( * ) Notice: Subject to any disclaimer, the term of this patent is extended or adjusted under 35 U.S.C. 154(b) by 0 days.

(21) Appl. No.: 15/088,539

(22) Filed: Apr. 1, 2016

(65) Prior Publication Data

US 2016/0243115 A1 Aug. 25, 2016

Related U.S. Application Data

(63) Continuation of application No. 11/813,662, filed as application No. PCT/IB2006/000026 on Jan. 10, 2006, now abandoned.

(60) Provisional application No. 60/643,055, filed on Jan. 10, 2005.

(51) Int. Cl.
*A61K 31/496* (2006.01)
*A61K 45/06* (2006.01)

(52) U.S. Cl.
CPC ............ *A61K 31/496* (2013.01); *A61K 45/06* (2013.01)

(58) Field of Classification Search
None
See application file for complete search history.

(56) References Cited

U.S. PATENT DOCUMENTS 6,040,307 A * 3/2000 Gray .................... A61K 31/495
514/254.07

FOREIGN PATENT DOCUMENTS

WO 94/14446 A1 7/1994

OTHER PUBLICATIONS

Sonino et al., Ketoconazole treatment in Cushing's syndrome: experience in 34 patients, Clin Endocrinol (Oxf). Oct. 1991;35(4):347-52 (Abstract).*
Loli et al., Use of ketoconazole in the treatment of Cushing's syndrome, J Clin Endocrinol Metab. Dec. 1986;63(6):1365-71 (Abstract).*
Rotstein et al., Stereoisomers of Ketoconazole: Preparation and Biological Activity, J. Med. Chem. (1992) 35, 2818-2825).*
Ma et al., "Hepatotoxicity and toxicokinetics of ketoconazole in rabbits." Acta Pharmacol Sin 2003; 24(8): 778-782.*

* cited by examiner

*Primary Examiner* — Svetlana M Ivanova
(74) *Attorney, Agent, or Firm* — Reed Smith LLP; Matthew S. Gibson

(57) ABSTRACT

Pharmaceuticals compositions comprising the 2S, 4R, ketoconazole enantiomer or its pharmaceutically acceptable salts, hydrates, and solvates, that are substantially free of the 2R, 4S ketoconazole enantiomer are useful to reduce cortisol synthese and for the treatment of type 2 diabetes, hyperglycemia, obesity, insulin resistance, dyslipidemia, hyperlipidemia, hypertension, Metabolic Syndrome, and other diseases and conditions, including but not limited to Cushing's Syndrome, depression, and glaucoma.

2 Claims, 7 Drawing Sheets

METHODS AND COMPOSITIONS FOR TREATING DIABETES, METABOLIC SYNDROME AND OTHER CONDITIONS

CROSS-REFERENCE TO RELATED APPLICATIONS

The present application is a continuation of still pending U.S. application Ser. No. 11/813,662, filed May 21, 2008, which is the United States national stage of International Application No. PCT/IB2006/000026, filed Jan. 10, 2006, which claims benefit of U.S. Provisional Application No. 60/643,055, filed Jan. 10, 2005, both of which are herein incorporated by reference in their entirety.

FIELD OF THE INVENTION

The present invention relates to pharmaceutical compositions and methods for treating diabetes and other conditions, including type 2 diabetes mellitus, metabolic syndrome, insulin resistance, obesity, lipid disorders, metabolic disease, and other conditions that can be treated by reducing cortisol synthesis, including but not limited to Cushing's Syndrome, osteoporosis, glaucoma and depression. The invention therefore relates to the fields of chemistry, biology, pharmacology, and medicine.

BACKGROUND OF THE INVENTION

Ketoconazole, 1-acetyl-4-[4-[[2-(2,4-dichlorophenyl)-2-[(1H-imidazol-1-yl)-methyl]-1,3-dioxolan-4-yl]methoxy]phenyl]piperazine, is a racemic mixture of the cis enantiomers (−)-(2S,4R) and (+)-(2R,4S) marketed as an anti-fungal agent. Ketoconazole inhibits fungal growth through the inhibition of ergosterol synthesis. Ergosterol is a key component of fungal cell walls.

More recently, ketoconazole was found to decrease plasma cortisol and to be useful, alone and in combination with other agents, in the treatment of a variety of diseases and conditions, including type 2 diabetes, Metabolic Syndrome (also known as the Insulin Resistance Syndrome, Dysmetabolic Syndrome or Syndrome X), and other medical conditions that are associated with elevated cortisol levels. See U.S. Pat. Nos. 5,584,790; 6,166,017; and 6,642,236, each of which is incorporated herein by reference. Cortisol is a stress-related hormone secreted from the cortex of the adrenal glands. ACTH (adenocorticotropic hormone) increases cortisol secretion. ACTH is secreted by the pituitary gland, a process activated by secretion of corticotropin releasing hormone (CRH) from the hypothalamus.

Cortisol circulates in the bloodstream and activates specific intracellular receptors, such as the glucocorticoid receptor (GR). Disturbances in cortisol levels, synthetic rates or activity have been shown to be associated with numerous metabolic complications, including insulin resistance, obesity, diabetes and Metabolic Syndrome. Additionally, these metabolic abnormalities are associated with substantially increased risk of cardiovascular disease, a major cause of death in industrialized countries. See Mårin P et al., "Cortisol secretion in relation to body fat distribution in obese premenopausal women." *Metabolism* 1992; 41:882-886, Bjorntorp, "Neuroendocrine perturbations as a cause of insulin resistance." *Diabetes Metab Res Rev* 1999; 15(6): 427-41, and Rosmond, "Role of stress in the pathogenesis of the metabolic syndrome." *Psychoneuroendocrinology* 2005; 30(1): 1-10, each of which is incorporated herein by reference.

While ketoconazole is known to inhibit some of the enzymatic steps in cortisol synthesis, such as, for example, 17α hydroxylase (Wachall et al., "Imidazole substituted biphenyls: a new class of highly potent and in vivo active inhibitors of P450 17 as potential therapeutics for treatment of prostate cancer." *Bioorg Med Chem* 1999; 7(9): 1913-24, incorporated herein by reference) and 11β-hydroxylase (Rotstein et al., "Stereoisomers of ketoconazole: preparation and biological activity." *J Med Chem* 1992; 35(15): 2818-25) and 11β-hydroxy steroid dehydrogenase (11β-HSD) (Diederich et al., "In the search for specific inhibitors of human 11β-hydroxysteroid-dehydrogenases (11β-HSDs): chenodeoxycholic acid selectively inhibits 11μ-HSD-L" *Eur J Endocrinol* 2000; 142(2): 200-7, incorporated herein by reference) the mechanisms by which ketoconazole decreases cortisol levels in the plasma have not been reported. For example, there is uncertainty regarding the effect of ketoconazole on the 11β-hydroxy steroid dehydrogenase (11β-HSD) enzymes. There are two 11β-HSD enzymes. One of these, 11β-HSD-I, is primarily a reductase that is highly expressed in the liver and can convert the inactive 11-keto glucocorticoid to the active glucocorticoid (cortisol in humans and corticosterone in rats). In contrast, the other, 11β-HSD-II, is primarily expressed in the kidney and acts primarily as an oxidase that converts active glucocorticoid (cortisol in humans and corticosterone in rats) to inactive 11-keto glucocorticoids. Thus, the plasma concentration of active glucocorticoid is influenced by the rate of synthesis, controlled in part by the activity of adrenal 11β-hydroxylase and by the rate of interconversion, controlled in part by the relative activities of the two 11β-HSD enzymes. Ketoconazole is known to inhibit these three enzymes (Diederich et al., supra) and the 2S,4R enantiomer is more active against the adrenal 11β-hydroxylase enzyme than is the 2R,4S enantiomer (Rotstein et al., supra). However, there are no reports describing the effect of the two ketoconazole enantiomers on either of 11β-HSD-I or 11β-HSD-II, so it is not possible to predict what effects, if any, the two different ketoconazole enantiomers will each have on plasma levels of the active glucocorticoid levels in a mammal.

Ketoconazole has also been reported to lower cholesterol levels in humans (Sonino et al. (1991). "Ketoconazole treatment in Cushing's syndrome: experience in 34 patients." *Clin Endocrinol (Oxf)*. 35(4): 347-52; Gylling et al. (1993). "Effects of ketoconazole on cholesterol precursors and low density lipoprotein kinetics in hypercholesterolania." *J Lipid Res.* 34(1): 59-67) each of which is incorporated herein by reference). The 2S,4R enantiomer is more active against the cholesterol synthetic enzyme 14αlanosterol demethylase than is the other (2R,4S) enantiomer (Rotstein et al infra). However, because cholesterol level in a human patient is controlled by the rate of metabolism and excretion as well as by the rate of synthesis it is not possible to predict from this whether the 2S,4R enantiomer of ketoconazole will be more effective at lowering cholesterol levels.

The use of ketoconazole as a therapeutic is complicated by the effect of ketoconazole on the P450 enzymes responsible for drug metabolism. Several of these P450 enzymes are inhibited by ketoconazole (Rotstein et al., supra). This inhibition leads to an alteration in the clearance of ketoconazole itself (Brass et al., "Disposition of ketoconazole, an oral antifungal, in humans." *Antimicrob Agents Chemother* 1982; 21(1): 151-8, incorporated herein by reference) and several other important drugs such as Glivec (Dutreix et al., "Pharmacokinetic interaction between ketoconazole and imatinib mesylate (Glivec) in healthy subjects." *Cancer*

*Chemother Pharmacol* 2004; 54(4): 290-4) and methylprednisolone (Glynn et al., "Effects of ketoconazole on methylprednisolone pharmacokinetics and cortisol secretion." *Clin Pharmacol Ther* 1986; 39(6): 654-9). As a result, the exposure of a patient to ketoconazole increases with repeated dosing, despite no increase in the amount of drug administered to the patient. This exposure and increase in exposure can be measured and demonstrated using the "Area under the Curve" (AUC) or the product of the concentration of the drug found in the plasma and the time period over which the measurements are made. The AUC for ketoconazole following the first exposure is significantly less than the AUC for ketoconazole after repeated exposures. This increase in drug exposure means that it is difficult to provide an accurate and consistent dose of the drug to a patient. Further, the increase in drug exposure increases the likelihood of adverse side effects associated with ketoconazole use.

Rotstein et al. (Rotsatin et al., supra) have examined the effects of the two ketoconazole cis enantiomers on the principal P450 enzymes responsible for drug metabolism and reported " . . . almost no selectivity was observed for the ketoconazole isomers" and, referring to drug metabolizing P450 enzymes: "[t]he IC50 values for the cis enantiomers were similar to those previously reported for racemic ketoconazole". This report indicated that both of the cis enantiomers could contribute significantly to the AUC problem observed with the ketoconazole racemate.

One of the adverse side effects of ketoconazole administration exacerbated by this AUC problem is liver reactions. Asymptomatic liver reactions can be measured by art increase in the level of liver specific enzymes found in the serum and an increase in these enzymes has been noted in ketoconazole treated patients (Sohn, "Evaluation of ketoconazole." *Clin Pharm* 1982; 1(3): 217-24, and Janssen and Symoens, "Hepatic reactions during ketoconazole treatment." *Am J Med* 1983; 74(1B): 80-5, each of which is incorporated herein by reference). In addition 1:12,000 patients will have more severe liver failure (Smith and Henry, "Ketoconazole: an orally effective antifungal agent. Mechanism of action, pharmacology, clinical efficacy and adverse effects." *Pharmacotherapy* 1984; 4(4): 199-204, incorporated herein by reference). As noted above, the amount of ketoconazole that a patient is exposed to increases with repeated dosing even though the amount of drug taken per day does not increase (the "AUC problem"). The AUC correlates with liver damage in rabbits (Ma et al., "Hepatotoxicity and toxicokinetics of ketoconazole in rabbits." *Acta Pharmacol Sin* 2003; 24(8): 778-782 incorporated herein by reference) and increased exposure to the drug is believed to increase the frequency of liver damage reported in ketoconazole treated patients.

Additionally, U.S. Pat. No. 6,040,307, incorporated herein by reference, reports that the 2S,4R enantiomer is efficacious in treating fungal infections. This same patent application also reports studies on isolated guinea pig hearts that show that the administration of racemic ketoconazole may be associated with an increased risk of cardiac arrhythmia, but provides no data in support of that assertion. However, as disclosed in that patent, arrhythmia had not been previously reported as a side effect of systemic racemic ketoconazole, although a particular subtype of arrhythmia, torsade de pointes, has been reported when racemic ketoconazole was administered concurrently with terfenadine. Furthermore several published reports (for example, Morganroth et al. (1997). "Lack of effect of azelastine and ketoconazole coadministration on electrocardiographic parameters in healthy volunteers." *J Clin Pharmacol.* 37(11): 1065-72) have demonstrated that ketoconazole does not increase the QTc interval. This interval is used as a surrogate marker to determine whether drugs have the potential for inducing arrhythmia. U.S. Pat. No. 6,040,307 also makes reference to diminished hepatoxicity associated with the 2S,4R enantiomer but provides no data in support of that assertion. The method provided in U.S. Pat. No. 6,040,307 does not allow for the assessment of hepatoxicity as the method uses microsomes isolated from frozen tissue.

Thus, there remains a need for new therapeutic agents and methods for treating diseases and conditions associated with elevated cortisol levels or activity or that may be treated by lowering cortisol level or activity that are as effective as ketoconazole but do not present, or present to a lesser degree, the issues of drug interactions and adverse side effects of ketoconazole. The present invention meets these and other needs.

SUMMARY OF THE INVENTION

The present invention arises in part from the discoveries that the 2S,4R enantiomer is more effective per weight unit than racemic ketoconazole or the 2R,4S enantiomer (the other enantiomer in the racemate) at reducing the concentration of the active glucocorticoid in the plasma and that the 2S,4R enantiomer does not lead to drug accumulation (or accumulates to a significantly less extent) as does racemic ketoconazole.

In a first aspect, the present invention provides methods for treating diseases and conditions associated with elevated cortisol levels, production rates or activity and other diseases and conditions that can be treated by reducing cortisol, or diseases or conditions that can be treated by reducing cholesterol levels, production rates or activity by administering a pharmaceutical composition containing a therapeutically effective amount of the 2S,4R ketoconazole enantiomer substantially or entirely free of the 2R,4S ketoconazole enantiomer.

In a second aspect, the present invention provides pharmaceutical compositions comprising a pharmaceutically acceptable carrier and a therapeutically effective amount of the 2S,4R ketoconazole enantiomer substantially or entirely free of the 2R,4S ketoconazole enantiomer formulated for use in the methods of the invention.

DETAILED DESCRIPTION OF THE INVENTION

Figure 1:
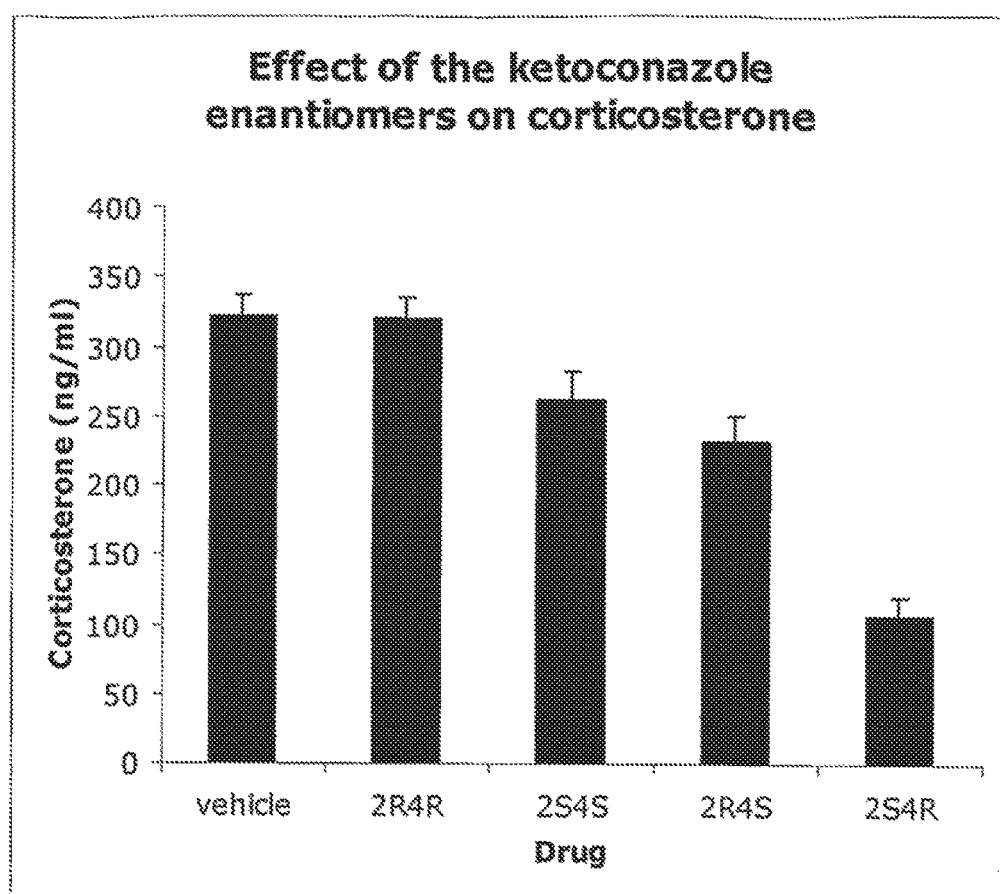
FIG. 1 shows the effect of the four ketoconazole enantiomers 2S,4S, 2R,4R, 2R,4S, and 2S,4R on plasma corticosterone. The figure shows that the 2S,4R enantiomer is more effective at lowering corticosterone than any of the other three enantiomers. The concentration of corticosterone in the plasma of Sprague-Dawley rats was determined four hours after delivery by oral gavage of 200 mg/kg of the indicated enantiomer.

The present invention provides pharmaceutical compositions comprising the 2S,4R ketoconazole enantiomer substantially or entirely free of the 2R,4S enantiomer, and methods of using such compositions. Substantially free of the 2R,4S enantiomer, in one embodiment, means that the ketoconazole content of the pharmaceutical composition is less than 2% of the 2R,4S enantiomer and more than 98% of the 2S,4R enantiomer. In another embodiment, substantially free of the 2R,4S enantiomer means the ketoconazole content of the pharmaceutical composition is less than 10% of the 2R,4S enantiomer and more than 90% of the 2S,4R enantiomer. In another embodiment, substantially free of the 2R,4S enantiomer means that the ketoconazole content of the pharmaceutical composition is less than 20% of the 2R,4S enantiomer and more than 80% of the 2S,4R enantiomer. The present invention also provides methods for treating diseases and conditions associated with elevated cortisol levels or activity and diseases and conditions that may be medically treated by reducing cortisol levels and cortisol activity with these pharmaceutical compositions. To aid in understanding the invention, this detailed description is organized as follows. Section I describes methods for preparing the 2S,4R enantiomer, its solvates and salts, and pharmaceutical compositions comprising it. Section II describes unit dosage forms of the pharmaceutical compositions of the invention and methods for administering them. Section III describes methods for treating diseases and conditions by administration of the 2S,4R ketoconazole enantiomer and pharmaceutical compositions comprising the 2S,4R ketoconazole enantiomer substantially free of the 2R,4S enantiomer.

I. Preparation of the 2S,4R Ketoconazole Enantiomer and Pharmaceutical Compositions containing the 2S,4R Ketoconazole Enantiomer Substantially or Entirely Free of the 2R,4S Ketoconazole Enantiomer As used herein, a composition containing "the 2S,4R ketoconazole enantiomer substantially or entirely free of the 2R,4S ketoconazole enantiomer" includes compositions that do not contain the 2R,4S ketoconazole enantiomer as well as compositions that contain substantially less of the 2R,4S ketoconazole enantiomer, relative to the amount of the 2S,4R enantiomer, than do racemic ketoconazole compositions currently approved for therapeutic use. Compositions useful in the methods of the invention include, for example and without limitation, compositions in which the total ketoconazole content is comprised of at least 80%, or at least 90%, or at least 99%, or at least 99.5%, or at least 99.9% or greater of the 2S,4R enantiomer.

The 2S,4R enantiomer of ketoconazole may be obtained by optical resolution of racemic ketoconazole. Such resolution can be accomplished by any of a number of resolution methods well known to a person skilled in the art, including but not limited to those described in Jacques et al., "Enantiomers, Racemates and Resolutions," Wiley, New York (1981), incorporated herein by reference. For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired enantiomer. Yet another method for obtaining compositions of the 2S,4R enantiomer substantially free of the 2R,4S enantiomer is a fractional crystallization of the diastereomeric salt of ketoconazole with (+)-camphor-10-sulfonic acid.

The 2S,4R enantiomer of ketoconazole can also be prepared directly by a variety of methods known to those of skill in the art. For example, the 2S,4R enantiomer can be prepared directly by transketolization reactions between 2-bromo-2',4'-dichloroacetophenone and optically pure solketal tosylates, as described by Rotstein et al. (Rotstein et al., supra, incorporated herein by reference).

The present invention also provides a variety of pharmaceutically acceptable salts of the 2S,4R enantiomer of ketoconazole for use in the pharmaceutical compositions of the invention. The term "pharmaceutically acceptable salt" refers to salts prepared from pharmaceutically acceptable bases or acids, including inorganic or organic bases and inorganic or organic acids. Salts derived from inorganic bases include aluminum, ammonium, calcium, copper, ferric, ferrous, lithium, magnesium, manganic, manganous, potassium, sodium, and zinc salts, and the like. The ammonium, calcium, magnesium, potassium, and sodium salts, in particular, can be preferred for some pharmaceutical formulations. Salts in the solid form can exist in more than one crystal structure and can also be in the form of hydrates and polyhydrates. The solvates, and, in particular, the hydrates of the 2S,4R ketoconazole enantiomer are useful in the preparation of the pharmaceutical compositions of the present invention.

Salts derived from pharmaceutically acceptable organic bases include salts of primary, secondary and tertiary amines, substituted amines, including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine, and the like.

When the compound to be formulated is basic, salts can be prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acid, and the like. Illustrative pharmaceutically acceptable acids include citric, hydrobromic, hydrochloric, maleic, phosphoric, sulfuric, and tartaric acids. Ketoconazole compounds are often basic, because the triazole ring is basic. The 2S,4R ketoconazole compound can be made and handled as a non-pharmaceutically acceptable salt (e.g. trifluoroacetate salts) during synthesis and then converted as described herein to a pharmaceutically acceptable salt.

Suitable pharmaceutically acceptable salts of the 2S,4R ketoconazole enantiomer include, but are not limited to, the mesylate, maleate, fumarate, tartrate, hydrochloride, hydrobromide, esylate, p-toluenesulfonate, benzoate, acetate, phosphate, and sulfate salts. For the preparation of pharmaceutically acceptable acid addition salts of the compound of 2S,4R ketoconazole, the free base can be reacted with the desired acids in the presence of a suitable solvent by conventional methods. Similarly, an acid addition salt can be converted to the free base form by methods known to those of skill in the art.

Pharmaceutical compositions of the invention can include metabolites of the 2S,4R ketoconazole enantiomer that are therapeutically active or prodrugs of the enantiomer. Prodrugs are compounds that are converted to therapeutically active compounds as they are being administered to a patient or after they have been administered to a patient.

Thus, the pharmaceutical compositions of the invention comprise the 2S,4R ketoconazole enantiomer, or a pharmaceutically acceptable salt, hydrate or solvate thereof, or a prodrug or active metabolite thereof, in combination with a pharmaceutically acceptable carrier and substantially or entirely free of the 2R,4S enantiomer. In one embodiment, the pharmaceutical composition contains a therapeutically effective amount of the 2S,4R anantiomer of ketoconazole or a pharmaceutically acceptable salt thereof and a pharmaceutically acceptable carrier. As noted above, pharmaceutically acceptable salts of the 2S,4R enantiomer useful in such compositions include, but are not limited to, the hydrochloride, phosphate, maleate, fumarate, tartrate, mesylate, esylate, and sulfate salts.

The "therapeutically effective amount" of the 2S,4R enantiomer of ketoconazole or pharmaceutically acceptable salt thereof will depend on the condition to be treated, the route and duration of administration, the physical attributes of the patient, including weight and other medications taken concurrently, and may be determined according to methods well known to those skilled in the art in light of the present disclosure (see Section II, below). The pharmaceutical compositions of the invention can be conveniently prepared in unit dosage form by methods well-known in the art of pharmacy as medicaments to be administered orally, parenterally (including subcutaneous, intramuscular, and intravenous administration), ocularly (ophthalmic administration), rectally, pulmonarily (nasal or oral inhalation), topically, transdermally or via buccal transfer.

The pharmaceutical compositions of the invention can be prepared by combining the 2S,4R ketoconazole enantiomer with a selected pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are typically preferred over oral liquid preparations.

Thus, in one embodiment, the pharmaceutically acceptable carrier is a solid and the pharmaceutical composition is a tablet for oral administration. Other suitable forms of the pharmaceutical compositions of the invention for oral administration include compressed or coated pills, dragees, sachets, hard or soft gelatin capsules, sublingual tablets, syrups and suspensions. The oral solid dosage forms may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and/or a sweetening agent such as sucrose, lactose, or saccharin. Capsules may also contain a liquid carrier such as a fatty oil. Various other materials may be present to act as coatings or to modify the physical form of the dosage unit. For instance, tablets may be coated with shellac, sugar or both. Tablets may be coated by standard aqueous or nonaqueous techniques. The typical percentage of active compound in these compositions may, of course, be varied from, for example and without limitation, about 2 percent to about 60 percent on a w/w basis.

In another embodiment, the pharmaceutically acceptable carrier is a liquid, and the pharmaceutical composition is intended for oral administration. Oral liquids suitable for use in such compositions include syrups and elixirs and can contain, in addition to the active ingredient, sucrose as a sweetening agent, methyl and propylparabens as preservatives, a dye, and/or a flavoring, such as cherry or orange flavor.

In another embodiment, the present invention provides a pharmaceutical composition of the 2S,4R ketoconazole enantiomer suitable for parenteral administration. For parenteral administration, the pharmaceutical composition is typically contained in ampoules or vials and consists essentially of an aqueous or non-aqueous solution or emulsion.

These compositions are typically in the form of a solution or suspension, and are typically prepared with water, and optionally include a surfactant such as hydroxypropylcellulose. Dispersions can be prepared in glycerol, liquid polyethylene glycols, and mixtures thereof in oils. Typically, preparations that are in diluted form also contain a preservative.

In another embodiment, the pharmaceutically acceptable carrier is a liquid, and the pharmaceutical composition is an injectable solution. The pharmaceutical injectable dosage forms, including aqueous solutions and dispersions and powders for the extemporaneous preparation of injectable solutions or dispersions, are also sterile and, at the time of administration, are sufficiently fluid for easy syringability. These compositions are stable under the conditions of manufacture and storage and are typically preserved. The carrier thus includes the solvent or dispersion medium containing, for example, water, ethanol, polyol (e.g. glycerol, propylene glycol and liquid polyethylene glycol), suitable mixtures thereof, and vegetable oils.

In another embodiment, the pharmaceutically acceptable carrier is a gel, and the pharmaceutical composition is provided in the form of a suppository. For rectal administration, the pharmaceutical composition is provided in a suppository, and the pharmaceutical acceptable carrier is a hydrophilic or hydrophobic vehicle. In another embodiment, the pharmaceutical composition useful in the methods of the invention is prepared for topical application, and the 2S,4R ketoconazole enantiomer is formulated as an ointment. The 2S,4R enantiomer can also be administered transdermally; suitable transdermal delivery systems are known in the art.

The pharmaceutical compositions of the invention also include sustained release compositions. Suitable sustained release compositions include those described in U.S. patent application publication Nos. 20050013834; 20030190357; and 2002055512 and PCT patent application publication Nos. WO 03011258 and 0152833, each of which is incorporated herein by reference.

II. Unit Dosage Forms; Frequency and Duration of Administration

As noted above, any suitable route of administration can be employed for providing a mammal, typically a human, but mammals of veterinary importance, such as cattle, horses, pigs, sheep, dogs, and cats, can also benefit from the methods described herein, with a therapeutically effective dose of the 2S,4R enantiomer. For example, oral, rectal, topical, parenteral, ocular, pulmonary, or nasal administration can be employed. Dosage forms include tablets, troches, dispersions, suspensions, solutions, capsules, creams, ointments, aerosols and the like. In many embodiments of the treatment methods of the invention, the pharmaceutical composition is administered orally. The therapeutically effective dosage of the active ingredient varies depending on the particular compound employed (salt, solvate, prodrug, or metabolite), the mode of administration, the condition being treated, and the severity of the condition. Such dosages may be ascertained readily by a person skilled in the art in light of the disclosure herein.

When treating or preventing the diseases and conditions as described herein, satisfactory results can obtained when the 2S,4R ketoconazole enantiomer is administered at a daily dosage of from about 0.1 to about 25 milligrams (mg) per kilogram (mpk) of body weight, preferably given as a single daily dose or in divided doses about two to six times a day. For oral administration to a human adult patient, the therapeutically effective amount will generally be administered in the range of 50 mg to 800 mg per dose, including but not limited to 100 mg per dose, 200 mg per dose, and 400 mg per dose, and multiple, usually consecutive daily doses will be administered in a course of treatment. The 2S,4R ketoconazole enantiomer pharmaceutical composition can be administered at different times of the day. In one embodiment the optimal therapeutic dose can be administered in the evening. In another embodiment the optimal therapeutic dose can be administered in the morning. The total daily dosage of the 2S,4R ketoconazole enantiomer thus can in one embodiment range from about 10 mg to about 2 g, and often ranges from about 10 mg to about 1 g, and most often ranges from about 100 mg to about 500 mg. In the case of a typical 70 kg adult human, the total daily dose of the 2S,4R ketoconazole enantiomer can range from about 10 mg to about 1000 mgs and will often range, as noted above, from about 50 mg to about 800 mg. This dosage may be adjusted to provide the optimal therapeutic response.

In one embodiment, the unit dosage form is suitable for oral administration and contains one or more pharmaceutical excipients. Examples of pharmacologically inactive excipients that can be included in an orally available formulation of the 2S,4R enantiomer of ketoconazole for purposes of the present invention and their function are provided in the following table.

| Inactive Ingredient | Trade Name | Grade | Function |
|---|---|---|---|
| Silicified Microcrystalline Cellulose | Prosolv HD 90 | NF | Diluent |
| Lactose Monohydrate | Modified, 316 Fast Flo | NF | Diluent |
| Corn Starch | STA-Rx | NF | Disintegrant |
| Magnesium Stearate | N/A | NF | Lubricant |
| Colloidal Silicon Dioxide | Cab-O-Sil M5P | NF | Glidant |

The excipients listed in the preceding table can be combined in varying proportion with the 2S,4R enantiomer to obtain specific drug tablet and manufacturing characteristics. The drug tablet size can vary from 1 mg total weight to 1000 mg total weight; for example and without limitation, from 100 mg total weight to 800 mg total weight. The proportion of the 2S,4R enantiomer present in the drug tablet can vary from 1% to 100%; for example and without limitation, from 10% to 90%. An example of a 400 mg tablet with the 2S,4R enantiomer comprising 50% of the tablet weight is provided in the following table. In this example, dry blends were made with the (−) cis 2S,4R ketoconazole and the listed inactive excipients and pressed as a dry blend into tablets.

| Component | % w/w | Tablet Weight (mg) |
|---|---|---|
| (—)cis 2S,4R Ketoconazole | 50.0 | 200 |
| Lactose Monohydrate, NF | 22.4 | 89.6 |
| Silicified Microcrystalline Cellulose, NF | 16.5 | 66.0 |
| Corn Starch, NF | 10.0 | 40.0 |
| Colloidal Silicon Dioxide, NF) | 0.5 | 2.0 |
| Magnesium Stearate, NF | 0.6 | 2.4 |
| Total | 100.0 | 400.0 |

A drug tablet formulation for 2S,4R ketoconazole was described in U.S. Pat. No. 6,040,307. This formulation included the active drug substance, (−) ketoconazole, Lactose, Cornstarch, water and Magnesium Stearate. Wet granules were generated with the ketoconazole, lactose, water and corn starch, these granules were dried in an oven prior to compressing into tablets with magnesium stearate and more corn starch. Tablets were compressed and dried. This is a less optimal method than the method of the invention described above using a dry blend process, as excess water and elevated temperatures are not introduced. Ketoconazole can undergo degradation (oxidation) (Farhadi and Maleki (2001). "A new spectrophotometric method for the determination of ketoconazole based on the oxidation reactions." *Analytical Sciences* 17 Supplement, i867-i869. The Japan Society for Analytical Chemistry), and oxidation reactions are accelerated in the presence of water and elevated temperatures.

The solid unit dosage forms of the pharmaceutical compositions of the invention contain the 2S,4R ketoconazole enantiomer or a salt or hydrate thereof in an amount ranging from about 1 mg to about 2 g, often from about 1.0 mg to about 1.0 g, and more often from about 10 mg to about 500 mg. In the liquid pharmaceutical compositions of the invention suitable for oral administration, the amount of the 2S,4R ketoconazole enantiomer can range from about 1 mg/ml to about 200 mg/ml. The therapeutically effective amount can also be an amount ranging from about 10 mg/ml to about 100 mg/ml. In one embodiment, the dose of the liquid pharmaceutical composition administered is an amount between 0.5 ml and 5.0 ml. In another embodiment, the dose is between about 1 ml and 3 ml. In the liquid pharmaceutical compositions of the invention designed for intravenous or subcutaneous administration the amount of the 2S,4R ketoconazole the amount of the 2S,4R enantiomer can range from about 0.01 to 1 mg/ml and can be administered at a rate of between 0.01 to 1 ml/minute by either a subcutaneous or intravenous administration. Alternatively the amount of the 2S,4R enantiomer can range from about 0.1 mg/ml to 10 mg/ml and can be administered at a rate of between 0.001 ml/minute to 0.1 ml/minute by either of a subcutaneous or intravenous administration.

As noted above, the pharmaceutical compositions of the invention will typically be administered for multiple consecutive days for periods ranging from one or more weeks to one, several, or many months (e.g., at least 7, 14, 28, 60 or 120 days). In one embodiment, the pharmaceutical compositions of the invention are administered for the treatment of a chronic disease, condition, or indication for treatment periods ranging from one month to twelve months. In another embodiment, the 2S,4R enantiomer is administered from one year to five years. In another embodiment, the 2S,4R enantiomer is administered from 5 years to 20 years. In another embodiment, the 2S,4R enantiomer is administered until there is remission from the disease or for the life of the patient.

The duration of administration in accordance with the methods of the invention depends on the disease or condition to be treated, the extent to which administration of the pharmaceutical composition has ameliorated the disease symptoms and conditions, and the individual patient's reaction to the treatment.

III. Methods for Treating Diseases and Conditions with the Pharmaceutical Compositions of the Invention
Inhibition of Cortisol Synthesis The 2S,4R enantiomer of ketoconazole is significantly more effective per weight unit at lowering the plasma concentration of physiologically active glucocorticoids than is either the racemic ketoconazole or the other enantiomer in racemic ketoconazole, the 2R,4S enantiomer. In addition, and as demonstrated in the Figures and in the Examples below, and as distinct from racemic ketoconazole, the 2S,4R enantiomer does not cause a time dependent increase in exposure to the 2S,4R enantiomer. Thus, the methods of the present invention offer significant therapeutic benefit over methods involving the administration of racemic ketoconazole in the treatment of diseases and conditions associated with elevated levels or aberrant activity of cortisol or in the treatment of diseases in which a benefit can be obtained by lowering normal cortisol levels or activity.

Cortisol promotes both the accumulation of adipose tissue and the release of free fatty acids from adipose tissue. When oxidized, free fatty acids act in an antagonistic manner to insulin in the liver, reducing insulin sensitivity in the liver (i.e., increasing hepatic insulin resistance). Cortisol also acts directly as an antagonist to the action of insulin in the liver, such that insulin sensitivity is further reduced. Cortisol also directly increases the amount of the rate limiting enzymes controlling glucose production by the liver. These actions result in increased gluconeogenesis and elevated levels of glucose production by the liver. Hepatic insulin resistance also results in impaired lipoprotein synthesis by the liver and so is a major contributing factor to the dyslipidemia known in patients with type 2 diabetes and in patients with Metabolic Syndrome. Patients who already have impaired glucose tolerance have a greater probability of developing type 2 diabetes in the presence of abnormally high levels of cortisol. High levels of cortisol can also lead to hypertension, in part through activation of the mineralocorticoid receptor. Inhibition of 11β-HSD-I enzyme shifts the ratio of cortisol and cortisone in specific tissues in favour of cortisone. The 2S,4R ketoconazole enantiomer is a cortisol synthesis inhibitor acting on the 11β hydroxylase enzyme and may also exert its therapeutic effect, at least in part, by inhibition of the 11β-HSD-I enzyme.

The present invention provides methods for using the 2S,4R enantiomer of ketoconazole, a cortisol synthesis inhibitor, for the treatment, control, amelioration, prevention, delay in the onset of or reduction of the risk of developing the diseases and conditions due at least in part to cortisol and/or other corticosteroids in a mammalian patient, particularly a human. In one embodiment, the method involves the administration of a therapeutically effective amount of the 2S,4R ketoconazole enantiomer or a pharmaceutically acceptable salt or solvate thereof, substantially or entirely free of other ketoconazole enantiomers, to the patient suffering from the disease or condition.

Cortisol activity can contribute to a large number of diseases and conditions, including, but not limited to, type 2 diabetes, metabolic syndrome, obesity, dyslipidemia, insulin resistance, and hypertension. These and other diseases and conditions susceptible to treatment with the compositions of the invention in accordance with the methods of the invention are described below.

Diabetes, Metabolic Syndrome, and Related Diseases and Conditions

Diabetes is caused by multiple factors and is most simply characterized by elevated levels of plasma glucose (hyperglycemia) in the fasting state. There are two generally recognized forms of diabetes: type 1 diabetes, in which patients produce little or no insulin, the hormone which regulates glucose production and utilization, and type 2 diabetes, in which patients produce insulin and even exhibit hyperinsulinemia (plasma insulin levels that may be similar or even elevated in comparison with non-diabetic subjects), while at the same time demonstrating hyperglycemia. Patients with type 2 diabetes typically have some degree of resistance to the glucose lowering actions of insulin. Type 1 diabetes is typically treated with exogenous insulin administered via injection.

However, patients with type 2 diabetes typically develop "insulin resistance", such that the effect of insulin in stimulating glucose and lipid metabolism in the main insulin-sensitive tissues, namely, muscle, liver, and adipose tissues, is diminished. Patients who are insulin resistant but do not have diabetes have elevated insulin levels that compensate for their insulin resistance, so that serum glucose levels are not elevated. In patients with type 2 diabetes, the plasma insulin levels, even when they are elevated, are insufficient to overcome the pronounced insulin resistance, resulting in hyperglycemia. Patients with type 2 diabetes may also have elevated circulating cortisol levels and/or production rates (see Lee et al., "Plasma insulin, growth hormone, cortisol, and central obesity among young Chinese type 2 diabetic patients." *Diabetes Care* 1999; 22(9): 1450-7; Homma et al., "Assessing systemic 11β-hydroxysteroid dehydrogenase with serum cortisone/cortisol ratios in healthy subjects and patients with diabetes mellitus and chronic renal failure." *Metabolism* 2001; 50(7): 801-4; and Richardson and Tayek, "Type 2 diabetic patients may have a mild form of an injury response: a clinical research center study." *Am J Physiol Endocrinol Metab* 2002; 282(6): E1286-90; Chiodini et a. "Association of subclinical hypercortisolism with type 2 diabetes mellitus: a case-control study in hospitalized patients." *Eur J Endocrinol* 2005; 153(6): 837-844; Liu et at "Elevated late-night salivary cortisol levels in elderly male type 2 diabetic veterans." *Clin Endocrinol (Oxf)* 2005; 63(6): 642-9; and Catargi et al. "Occult Cushing's syndrome in type-2 diabetes." *J Clin Endocrinol Metab* 2003; 88(12): 5808-13, each of which is incorporated herein by reference). Excess cortisol is now known (see U.S. Pat. No. 5,849,740, incorporated herein by reference) to induce insulin resistance and two prime characteristics of type 2 diabetes: reduced peripheral glucose uptake and increased hepatic glucose output. See also Rizza et al., "Cortisol-induced insulin resistance in man: impaired suppression of glucose production and stimulation of glucose utilization due to a postreceptor defect of insulin action." *J Clin Endocrinol Metab* 1982; 54(1): 131-8; Holmang and Bjorntorp, "The effects of cortisol on insulin sensitivity in muscle." *Acta Physiol Scand* 1992; 144(4): 425-31; Lecavalier et al., "Glucagon-cortisol interactions on glucose turnover and lactate gluconeogenesis in normal humans." *Am J Physiol* 1990; 258(4 Pt 1): E569-75; and Khani and-Tayek, "Cortisol increases gluconeogenesis in humans: its role in the metabolic syndrome." *Clin Sci (Lond)* 2001; 101(6): 739-47; each of which is incorporated herein by reference.

Persistent or uncontrolled hyperglycemia that occurs in diabetes is associated with increased morbidity and premature mortality. Abnormal glucose homeostasis is also associated both directly and indirectly with obesity, hypertension, and alterations in lipid, lipoprotein, and apolipoprotein metabolism. Patients with type 2 diabetes are at increased risk of cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism obesity, and hypertension are critically important in the clinical management and treatment of diabetes mellitus. The present invention provides methods for such therapeutic control by the administration of therapeutically effective amounts of the 2S,4R enantiomer of ketoconazole substantially or entirely free of the 2R,4S enantiomer.

Many patients who have insulin resistance but have not (yet) developed type 2 diabetes are also at a risk of developing a constellation of signs or symptoms previously referred to as the "Insulin Resistance Syndrome, Dysmetabolic Syndrome or Syndrome X", now more widely known as the "Metabolic Syndrome". Metabolic Syndrome is characterized by insulin resistance, along with abdominal obesity, hyperinsulinemia, high blood pressure, low HDL levels, high VLDL triglyceride and small dense LDL particles and elevated glucose levels. These patients, whether or not they develop overt diabetes mellitus, are at increased risk of developing the cardiovascular complications listed above. Patients with Metabolic Syndrome have been reported to have abnormalities in cortisol levels, production or catabolism (see Berceanu-Gabrielescu et al., "Hypercorticism—a risk factor in arterial hypertension and atherosclerosis." *Endocrinologie* 1981; 19(2): 123-7; Phillips et al., "Elevated plasma cortisol concentrations: a link between low birth weight and the insulin resistance syndrome?" *J Clin Endocrinol Metab* 1998; 83(3): 757-60; and Ward et al., "Cortisol and the metabolic syndrome in South Asians." *Clin Endocrinol (Oxf)* 2003; 58(4): 500-5; each of which is incorporated herein by reference).

Treatment of type 2 diabetes typically includes diet therapy and increased physical exercise either alone or in combination with pharmacologic therapy. Increasing the plasma level of insulin by administration of sulfonylureas (e.g. tolbutamide, and glipizide) or meglitinides, which stimulate the pancreatic beta cells to secrete more insulin, and/or by injection of insulin when sulfonylureas or meglitinides become ineffective, can result in insulin concentrations high enough to stimulate insulin-resistant tissues. However, dangerously low levels of plasma glucose can result, and an increased level of insulin resistance can ultimately occur.

Biguanides reduce excessive production of glucose by the liver and increase insulin sensitivity, resulting in some correction of hyperglycemia. However, many biguanides, e.g., phenformin and metformin, can cause lactic acidosis, nausea, and diarrhea.

The thiazolidinediones or glitazones (i.e. 5-benzylthiazolidine-2,4-diones) are a newer class of compounds that have been characterized as having potential for ameliorating hyperglycemia and other symptoms of type 2 diabetes. These agents increase insulin sensitivity in muscle, liver, and adipose tissue, resulting in partial or complete correction of the elevated plasma levels of glucose substantially without causing hypoglycemia. The glitazones that are currently marketed are agonists of the peroxisome proliferator activated receptor (PPAR) γ subtype. PPARγ agonism is generally believed to be responsible for the improved insulin sensitization that is observed with the glitazones. Newer PPAR agonists that are being developed for treatment of type 2 diabetes and/or dyslipidemia are agonists of one or more of the PPAR α, γ and δ subtypes. One disadvantage of all known glitazones is their weight-increasing effect, mediated via an increase in adipose tissue mass. Another disadvantage is that glitazones have been associated with an increased risk of heart failure, mediated via fluid retention.

There remains a need for new methods of treating diabetes and related conditions, such as the various conditions that individually and collectively contribute to Metabolic Syndrome. The present invention meets this need. The present invention provides a method of treating diabetes, and the related conditions of hyperglycemia and insulin resistance in a mammalian patient in need of such treatment, which method comprises administering to said patient a therapeutically effective amount of a pharmaceutical composition containing the 2S,4R enantiomer of ketoconazole substantially free of the 2R,4S enantiomer. In one embodiment, the method is used to treat type 2 diabetes. Administration of a therapeutically effective amount of an 11β-hydroxylase inhibitor such as the 2S,4R ketoconazole enantiomer substantially free of the 2R,4S enantiomer is effective in treating, controlling, and ameliorating the symptoms of diabetes, particularly type 2 diabetes, and administration of a therapeutically effective amount of an 11β-hydroxylase inhibitor such as the 2S,4R ketoconazole enantiomer substantially free of the 2R,4S enantiomer on a regular, daily basis can delay or prevent the onset of type 2 diabetes.

By reducing insulin resistance and maintaining serum glucose at normal concentrations, the pharmaceutical compositions of this invention also have utility in the treatment and prevention of conditions that accompany type 2 diabetes and insulin resistance, including obesity (typically abdominal obesity), Metabolic Syndrome ("Syndrome X"), including each of the symptoms and conditions that contribute to the syndrome, diabetic retinopathy, neuropathy, nephropathy, and premature cardiovascular disease.

Excessive levels of cortisol have been associated with obesity, which may be associated with the ability of cortisol to stimulate adipogenesis in general and visceral (also known as abdominal) obesity in particular. Visceral/abdominal obesity is closely associated with glucose intolerance, hyperinsulinemia, hypertriglyceridemia, and other factors (conditions and symptoms) of Metabolic Syndrome, such as high blood pressure, elevated VLDL and reduced HDL, as well as diabetes. Thus, the administration of an effective amount of an 11β-hydroxylase inhibitor such as the 2S,4R ketoconazole enantiomer substantially free of the 2R,4S enantiomer is useful in the treatment or control of obesity (e.g., abdominal obesity) and Metabolic Syndrome. Long-term treatment with an 11β-hydroxylase inhibitor such as the 2S,4R ketoconazole enantiomer substantially free of the 2R,4S enantiomer in accordance with the methods of the invention is also useful in delaying or preventing the onset of obesity, especially if the patient uses an 11β-hydroxylase inhibitor such as the 2S,4R ketoconazole enantiomer substantially free of the 2R,4S enantiomer in combination with controlled diet and exercise.

Thus, in another embodiment, the present invention provides a method of treating obesity (e.g., abdominal obesity) in a mammalian patient in need of such treatment, which method comprises administering to said patient a therapeutically effective amount of the 2S,4R ketoconazole enantiomer substantially free of the 2R,4S enantiomer. Likewise, in another embodiment, the present invention provides a method of treating Metabolic Syndrome in a mammalian patient in need of such treatment, which comprises administering to said patient a therapeutically effective amount of a pharmaceutical composition containing the 2S,4R ketoconazole enantiomer substantially free of the 2R,4S enantiomer.

Atherosclerosis, Lipid Disorders, Hypertension

Inhibition of 14α lanosterol demethylase and a reduction in cholesterol and inhibition of 11β-hydroxylase activity and a reduction in the amount of cortisol are beneficial in treating or controlling hypertension and dyslipidemia. Because hypertension and dyslipidemia contribute to the development of atherosclerosis, administration of a therapeutically effective amount of a 14α-lanosterol demethylase inhibitor and an 11β-hydroxylase inhibitor such as the 2S,4R ketoconazole enantiomer substantially free of the 2R,4S enantiomer can be beneficial in treating, controlling, delaying the onset of, or preventing hypertension, dyslipidemia, and atherosclerosis. In one embodiment, the invention provides a method of treating atherosclerosis in a mammalian patient in need of such treatment, said method comprising administering to said patient a therapeutically effective amount of a pharmaceutical composition containing the 2S,4R ketoconazole enantiomer substantially free of the 2R,4S enantiomer.

In another embodiment, the present invention provides a method of treating a lipid disorder selected from the group consisting of dyslipidemia, hyperlipidemia, hypertriglyceridemia, hypercholesterolemia, low HDL, and high LDL, in a mammalian patient in need of such treatment, such method comprising administering to said patient a therapeutically effective amount of a pharmaceutical composition containing the 2S,4R ketoconazole enantiomer substantially free of the 2R,4S enantiomer.

Stroke

Inhibition of 14α lanosterol demethylase and a reduction in cholesterol and inhibition of 11β-hydroxylase activity and a reduction in the amount of cortisol are beneficial in treating or ischemic stroke. Because cortisol, hypertension and dyslipidemia contribute to the severity and mortality of ischemic strokes, administration of a therapeutically effective amount of a 14α-lanosterol demethylase inhibitor and an 11β-hydroxylase inhibitor such as the 2S,4R ketoconazole enantiomer substantially free of the 2R,4S enantiomer can be beneficial in treating, or reducing the severity of ischemic strokes. In one embodiment, the invention provides a method of treating an ischemic stroke event in a patient in need of such treatment, said method comprising administering to said patient a therapeutically effective amount of a pharmaceutical composition containing the 2S,4R ketoconazole enantiomer substantially free of the 2R,4S enantiomer Alzheimer's Disease Inhibition of 14α lanosterol demethylase and a reduction in cholesterol and inhibition of 11β-hydroxylase activity and a reduction in the amount of cortisol are beneficial in treating or Alzheimer's disease. Because elevated cortisol has been associated with the development of Alzheimer's disease and a reduction in cholesterol through the use of statins may reduce the severity of Alzheimer's disease, administration of a therapeutically effective amount of a 14α-lanosterol demethylase inhibitor and an 11β-hydroxylase inhibitor such as the 2S,4R ketoconazole enantiomer substantially free of the 2R,4S enantiomer can be beneficial in treating, or reducing the severity of Alzheimer's disease. In one embodiment, the invention provides a method of treating Alzheimer's disease in a mammalian patient in need of such treatment, said method comprising administering to said patient a therapeutically effective amount of a pharmaceutical composition containing the 2S,4R ketoconazole enantiomer substantially free of the 2R,4S enantiomer.

Cognitive Impairment, Dementia, and Depression

Excessive levels of cortisol in the brain can also result in neuronal loss or dysfunction through the potentiation of neurotoxins. Cognitive impairment has been associated with aging and excess levels of cortisol in the brain (see Seckl Walker, "Minireview: 11β-hydroxysteroid dehydrogenase type 1—a tissue-specific amplifier of glucocorticoid action." *Endocrinology* 2001; 142(4): 1371-6, incorporated herein by reference). Administration of an effective amount of an 11β-hydroxylase inhibitor such as the 2S,4R ketoconazole enantiomer substantially free of the 2R,4S enantiomer results in the reduction, amelioration, control, or prevention of cognitive impairment associated with aging and of neuronal dysfunction. In one embodiment, the invention provides a method of treating cognitive impairment, neuronal dysfunction, and/or dementia in a mammalian patient in need of such treatment, said method comprising administering to said patient a therapeutically effective amount of a pharmaceutical composition of the 2S,4R ketoconazole enantiomer substantially free of the 2R,4S enantiomer.

Another condition in which high cortisol levels are reported to be causally important is depression. Muck-Seler et al. (Muck-Seler et al., "Platelet serotonin and plasma prolactin and cortisol in healthy, depressed and schizophrenic women." *Psychiatry Res* 2004; 127(3): 217-26, incorporated herein by reference) reported that plasma cortisol levels were significantly increased both in schizophrenic and in depressed patients compared with values in healthy controls. In one embodiment, the invention provides a method of treating depression in a mammalian patient in need of such treatment, said method comprising administering to said patient a therapeutically effective amount of a pharmaceutical composition of the 2S,4R ketoconazole enantiomer substantially free of the 2R,4S enantiomer.

Cushing's Syndrome

Cushing's Syndrome is a metabolic disease or condition in which patients have high cortisol levels in their blood stream. These high levels may result from adrenal gland malfunction due to a pituitary tumor or a secondary tumor, both producing the cortisol secretagogue ACTH in excess or be due to a tumor or disorder of the adrenal gland per se that directly overproduces cortisol. Patients with Cushing's syndrome often develop type 2 diabetes. Treatment of Cushing's Syndrome can involve removal of the offending tumor and/or treatment with cortisol synthesis inhibitors such as metyrapone, ketoconazole, or aminoglutethimide (see Murphy, "Steroids and depression." *J Steroid Biochem Mol Biol* 1991; 38(5): 537-59, incorporated herein by reference). In one embodiment, the present invention provides a method of treating Cushing's Syndrome in a patient in need of such treatment, which method comprises administering to said patient a therapeutically effective amount of a pharmaceutical composition of the 2S,4R ketoconazole enantiomer substantially free of the 2R,4S enantiomer, alone or in combination with another cortisol synthesis inhibitor, such as metyrapone or aminoglutethimide.

Decreased Insulin Secretion

Glucocorticoids have been shown to reduce insulin secretion in vivo (see Billaudel and Sutter, "Direct effect of corticosterone upon insulin secretion studied by three different techniques." *Horm Metab Res* 1979; 11(10): 555-60, incorporated herein by reference). Inhibition of cortisol synthesis as provided by the pharmaceutical compositions used in the methods of the invention can therefore be beneficial in the treatment of decreased insulin secretion. In addition, reduced 11beta-HSD-I activity has been observed, in isolated murine pancreatic beta cells, to improve glucose stimulated insulin secretion (see Davani et al., "Type 1 11beta-hydroxysteroid dehydrogenase mediates glucocorticoid activation and insulin release in pancreatic islets." *J Biol Chem* 2000; 275(45): 34841-4, incorporated herein by reference). In one embodiment, the invention provides a method of treating decreased insulin secretion in a mammalian patient in need of such treatment, said method comprising administering to said patient a therapeutically effective amount of a pharmaceutical composition of the 2S,4R ketoconazole enantiomer substantially free of the 2R,4S enantiomer.

Glaucoma and Intraocular Pressure

There is a connection between the levels of glucocorticoid target receptors and the 11□-HSD-I enzymes and the susceptibility to glaucoma (see Stokes at al., "Altered peripheral sensitivity to glucocorticoids in primary open-angle glaucoma." *Invest Ophthalmol Vis Sci* 2003; 44(12): 5163-7, incorporated herein by reference). High cortisol levels are reported to be causally important in glaucoma. Median total plasma, plasma free, and percent free cortisol levels are higher in patient with ocular hypertension and glaucoma. The most significant differences occurred with percent free cortisol values between normal and glaucomatous subjects (see Schwartz et al., "Increased plasma free cortisol in ocular hypertension and open angle glaucoma." *Arch Ophthalmol* 1987; 105(8): 1060-5, incorporated herein by reference).

In accordance with the methods of the present invention, inhibition of 11β-hydroxylase activity by the administration of the 2S,4R ketoconazole enantiomer substantially free of the 2R,4S enantiomer is useful in reducing intraocular pressure and in the treatment of glaucoma. In one embodiment, the invention provides a method of treating glaucoma and reducing intraocular pressure in a mammalian patient in need of such treatment, said method comprising administering to said patient a therapeutically effective amount of a pharmaceutical composition of the 2S,4R ketoconazole enantiomer substantially free of the 2R,4S enantiomer.

Immunomodulation

In certain disease states, such as tuberculosis, psoriasis, and even under conditions of excessive stress, high glucocorticoid activity shifts the immune response to a humoral response, when in fact a cell based response may be more beneficial to the patient. Inhibition of 11β-HSD-I activity and the attendant reduction in glucocorticoid levels shifts the immune response toward a cell based response (see Mason, "Genetic variation in the stress response: susceptibility to experimental allergic encephalomyelitis and implications for human inflammatory disease." Immunol Today 1991; 12(2): 57-60; and Rook, "Glucocorticoids and immune function." Baillieres Best Pract Res Clin Endocrinol Metab 1999; 13(4): 567-81; each of which is incorporated herein by reference). In one embodiment, the invention provides a method of modulating the immune response to a cell-based response in a mammalian patient in need of such treatment, said method comprising administering to said patient a therapeutically effective amount of a pharmaceutical composition of the 2S,4R ketoconazole enantiomer substantially free of the 2R,4S enantiomer.

Impaired Renal Function.

Increased intra-renal blood pressure can lead to renal damage. Cortisol can compete with true mineralocorticoids for access to the aldosterone receptor and increase blood pressure. Ketoconazole has been tested in patients with renal failure and has been shown to increase glomerular filtration rate. Ketoconazole has also been shown to decrease the leakage of albumin from kidneys in patients with diabetes type 2 without renal failure. Thus, in one embodiment the invention provides a method of treating impaired renal function or reducing albumin leakage in a mammalian patient in need of such treatment, said method comprising administering to said patient a therapeutically effective amount of a pharmaceutical composition of the 2S,4R ketoconazole enantiomer substantially free of the 2R,4S enantiomer Therapeutic Uses of the 2S,4R KetoconazoleEenantiorner In view of the foregoing, those of skill in the art will appreciate that the present invention provides a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, and (21) other conditions and disorders where insulin resistance is a component, in a mammalian patient in need of such treatment, said method comprising administering to the patient a therapeutically effective amount of a pharmaceutical composition of the 2S,4R ketoconazole enantiomer substantially free of the 2R,4S enantiomer.

In another aspect, the present invention provides a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, and (21) other conditions and disorders where insulin resistance is a component in a mammalian patient in need of such treatment, said method comprising administering to the patient a therapeutically effective amount of a pharmaceutical composition of the 2S,4R ketoconazole enantiomer substantially free of the 2R,4S enantiomer.

In another aspect, the present invention provides a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, and (21) other conditions and disorders where insulin resistance is a component in a mammalian patient in need of such treatment, said method comprising administering to the patient a therapeutically effective amount of a pharmaceutical composition of the 2S,4R ketoconazole enantiomer substantially free of the 2R,4S enantiomer.

Other Conditions

The invention provides a method for reducing plasma cortisol levels in a subject not diagnosed with or under treatment for a fungal infection, by administering a pharmaceutical composition comprising a pharmaceutically acceptable carrier and a therapeutically effective amount of 2S,4R ketoconazole enantiomer substantially free of the 2R,4S ketoconazole enantiomer to the subject. For example, the methods of the invention may also be used for treatment of diseases and conditions in which cortisol levels are not elevated (e.g., normal or below normal levels) but in whom therapeutic benefit can be obtained by reducing cortisol levels.

Additional Optional Subject Characteristics

In certain aspects of the invention, a patient being treated with a pharmaceutical composition comprising the 2S,4R ketoconazole enantiomer substantially free of the 2R,4S enantiomer is not diagnosed with and/or is not under treatment for a fungal infection. In certain aspects of the invention, a patient being treated with a pharmaceutical composition comprising the 2S,4R ketoconazole enantiomer substantially free of the 2R,4S enantiomer is not diagnosed with and/or is not under treatment for hypercholesterolemia.

In certain aspects of the invention, a patient being treated with a pharmaceutical composition of the 2S,4R ketoconazole enantiomer substantially free of the 2R,4S enantiomer is not diagnosed with and/or is not under treatment for one or more diseases, disorders, or conditions independently selected from the following: (1) hyperglycemia, (2) low glucose tolerance, (3) insulin resistance, (4) obesity, (5) a lipid disorder, (6) dyslipidemia, (7) hyperlipidemia, (8) hypertriglyceridemia, (9) hypercholesterolemia, (10) low HDL levels, (11) high LDL levels, (12) atherosclerosis (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) prostate cancer, (22) benign prostatic hyperplasia, and (23) other conditions and disorders where insulin resistance is a component.

Reducing Cortisol Levels in a Subject by Providing a Constant Exposure to 1-acetyl-4-[4-[[2-(2,4-dichlorophenyl)-2-[(1H-imidazol-1-yl)-methyl]-1,3-dioxolan-4-yl]methoxy]phenyl]piperazine In one aspect the invention provides a method of reducing cortisol levels in a subject by providing a constant exposure to 1-acetyl-4-[4-[[2-(2,4-dichlorophenyl)-2-[(1H-imidazol-1-yl)-methyl]-1,3-dioxolan-4-yl]methoxy]phenyl]piperazine by administering doses of 2S,4R enantiomer that are substantially free of the 2R,4S enantiomer to the patient. In this context, providing a constant exposure to 1-acetyl-4-[4-[[2-(2,4-dichlorophenyl)-2-[(1H-imidazol-1-yl)-methyl]-1,3-dioxolan-4-yl]methoxy]phenyl]piperazine means that the drug does not accumulate in the subject to whom the drug is administered.

In one embodiment the 2S,4R is administered over a period of at least 14 days (e.g., 14 days), and preferably at least 28 days (e.g., 28 days). In one embodiment, the doses of 2S,4R enantiomer are administered daily (as a single or multiple daily administration). In one embodiment, the doses of 2S,4R enantiomer are administered on alternate days. In one embodiment, the doses of 2S,4R enantiomer are administered according to an other schedule as part of a course of therapy, where the course of therapy lasts at least 28 days and where administration of an equal weight amount (or, alternatively, a double weight amount) of racemic ketoconazole results in accumulation of the drug in the subject.

Accumulation of drug, or the absence of accumulation, can be measured by determining the plasma level of drug on a first day and on a measuring the plasma level of the drug on one or more subsequent days. For example, if the plasma level is measured on a first day, denoted Day 1, subsequent measurements can be made on Day 7 and/or Day 14 and/or Day 28, or daily for 1, 2 or 4 weeks. In one embodiment, determining the plasma level involves measuring a 12 hour or 24 hour AUC. In one embodiment, the cortisol plasma level on Day 1 and on at least one subsequent day selected from Day 7, Day 14 and Day 28 differs by less than about 50%, preferably by less than about 25%, and sometimes by less than 15%. It will be appreciated that, guided by this disclosure, a constant exposure of a particular subject to 1-acetyl-4-[4-[[2-(2,4-dichlorophenyl)-2-[(1H-imidazol-1-yl)-methyl]-1,3-dioxolan-4-yl]methoxy]phenyl]piperazine can also be deduced from administration of doses shown in pharmacokinetic studies to result in constant exposure in a statistically significant number of similar subjects.

In a preferred embodiment, the constant exposure is provided by administering a constant total periodic dose of the 2S4R enantiomer, such as a constant total daily dose (in one or more administrations per day). In an embodiment, the subject has not previously been treated with racemic or enantiomeric ketoconazole. In one embodiment, the subject has not been administered drug for at least 14 days, at least 28 days, or at least 6 months prior to Day 1. In one embodiment the subject is a human patient. In another embodiment, the subject is a dog or is a Sprague-Dawley rat. In an embodiment, the subject is diagnosed with a condition characterized by elevated cortisol levels.

Combination Therapies

Thus, a variety of diseases, disorders, and conditions can be treated, controlled, prevented or delayed with the pharmaceutical compositions and methods of this invention, including but not limited to: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, and (21) other disorders where insulin resistance is a component. In one embodiment, a method of the invention is practiced on a patient who concurrently receives another treatment for one or more of these conditions.

As is apparent from the Figures and the Examples provided herein the 2S,4R enantiomer of ketoconazole does not alter the pharmacokinetics of the 2S,4R enantiomer and, by extension, the 2S,4R enantiomer of ketoconazole will not alter the pharmacokinetics of other drugs that are metabolized and excreted by the same pathways that are utilized by the 2S,4R enantiomer. Thus, the present invention provides for a method of co-administering drugs that are commonly co-administered with racemic ketoconazole without the risks of aberrant pharmacokinetics of the co-administered drug or racemic ketoconazole attendant to the administration of racemic ketoconazole.

The pharmaceutical compositions of the invention can be co-administered or otherwise used in combination with one or more other drugs in the treatment, prevention, suppression, or amelioration of the diseases, disorders, and conditions described herein as susceptible to therapeutic intervention in accordance with the methods of the invention. Typically, the combination of the drugs provided by the methods of the present invention is safer or more effective than either drug alone or of the non-2S,4R ketoconazole enantiomer drug in combination with racemic ketoconazole, or the combination is safer or more effective than would be expected based on the additive properties of the individual drugs. Such other drug(s) may be administered by a route and in an amount commonly used contemporaneously or sequentially with a pharmaceutical composition of the 2S,4R ketoconazole enantiomer substantially free of the 2R,4S enantiomer. When a pharmaceutical composition of the 2S,4R ketoconazole enantiomer substantially free of the 2R,4S enantiomer is used contemporaneously with one or more other drugs, a combination product containing such other drug(s) and the 2S,4R ketoconazole enantiomer can be utilized if the two active drugs can be coformulated. Combination therapy in accordance with the methods of the invention also includes therapies in which the pharmaceutical compositions useful in the methods of the invention and one or more other drugs are administered on different overlapping schedules. It is contemplated that, when used in combination with other active ingredients, the pharmaceutical compositions useful in the methods of the present invention or the other active ingredient or both may be used effectively in lower doses than when each is used alone. Accordingly, the pharmaceutical compositions useful in the methods of the present invention include those that contain one or more other active ingredients, in addition to the 2S,4R ketoconazole enantiomer.

Examples of other drugs that may be administered in combination with a pharmaceutical composition of the present invention, either separately or, in some instances, the same pharmaceutical composition, include, but are not limited to:

(a) dipeptidyl peptidase IV (DPP-IV) inhibitors; (b) insulin sensitizers including (i) PPARγ agonists such as the glitazones (e.g. pioglitazone, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin; (c) insulin, insulin analogs, or insulin mimetics;

(d) sulfonylureas and other insulin secretagogues such as tolbutamide, glipizide, glyburide, meglitinide, and related materials; (e) α-glucosidase inhibitors (such as acarbose); (f) glucagon receptor antagonists such as those disclosed in PCT patent application publication Nos. WO 98/04528, WO 99/01423, WO 00/39088, and WO 00/69810, each of which is incorporated herein by reference; (g) GLP-1, GLP-1 analogs and mimetics, and GLP-1 receptor agonists such as those disclosed in PCT patent application publication Nos. WO 00/42026 and WO 00/59887, each of which is incorporated herein by reference; (h) GIP, GIP analogs and mimetics, including but not limited to those disclosed in PCT patent application publication No. WO 00/58360, incorporated herein by reference, and GIP receptor agonists; (i) PACAP, PACAP analogs and mimetics, and PACAP receptor 3 agonists such as those disclosed in PCT patent application publication No. WO 01/23420, incorporated herein by reference; (j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as for example ezetimibe and β-sitosterol, (v) acyl CoA:cholesterol acyltransferase inhibitors, such as for example avasimibe, and (vi) anti-oxidants such as probucol; (k) PPARδ agonists, such as those disclosed in PCT patent application publication No. WO 97/28149, incorporated herein by reference; (l) antiobesity compounds such as fenfluramine, dexfenfluramine, phentermine, sibutramine, orlistat, neuropeptide Y5 inhibitors, CB1 receptor inverse agonists and antagonists, and β$_3$ adrenergic receptor agonists; (m) an ileal bile acid transporter inhibitor; (n) agents intended for use in inflammatory conditions other than glucocorticoids, such as aspirin, non-steroidal anti-inflammatory drugs, azulfidine, and cyclooxygenase 2 selective inhibitors, and (o) protein tyrosine phosphatase-1B (PTP-1B) inhibitors.

Thus, in one embodiment, the present invention provides a pharmaceutical composition that comprises: (1) a therapeutically effective amount of 2S,4R ketoconazole enantiomer substantially free of 2R,4S ketoconazole enantiomer; (2) a therapeutically effective amount of compound selected from the group consisting of: (a) DPP-IV inhibitors; (b) insulin sensitizers selected from the group consisting of (i) PPAR agonists and (ii) biguanides; (c) insulin and insulin analogs and mimetics; (d) sulfonylureas and other insulin secretagogues; (e) α-glucosidase inhibitors; (f) glucagon receptor antagonists; (g) GLP-1, GLP-1 analogs and mimetics, and GLP-1 receptor agonists; (h) GIP, GIP analogs and mimetics, and GIP receptor agonists; (i) PACAP, PACAP analogs and mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA: cholesterol acyltransferase inhibitors, and (viii) anti-oxidants; (k) PPARδ agonists; (l) antiobesity compounds; (m) an ileal bile acid transporter inhibitor, (n) anti-inflammatory agents other than glucocorticoids; and (o) protein tyrosine phosphatase-1B (PTP-1B) inhibitors; and (3) a pharmaceutically acceptable carrier.

The above pharmaceutical compositions and combination therapies include those in which the 2S,4R ketoconazole enantiomer substantially or entirely free of the 2R,4S enantiomer, or a pharmaceutically acceptable salt, hydrate, or solvate thereof; is coformulated or co-administered with one or more other active compounds. Non-limiting examples include combinations of the 2S,4R ketoconazole enantiomer with two or more active compounds selected from biguanides, sulfonylureas, HMG-CoA reductase inhibitors, PPAR agonists, PTP-1B inhibitors, DPP-IV inhibitors, and anti-obesity compounds.

Thus, in one embodiment, the present invention provides a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, and (21) other conditions and disorders where insulin resistance is a component, in a mammalian patient in need of such treatment, said method comprising administering to the patient therapeutically effective amounts of a pharmaceutical composition of the 2S,4R ketoconazole enantiomer substantially free of the 2R,4S enantiomer and of a compound or pharmaceutical composition comprising said compound selected from the group consisting of: (a) DPP-IV inhibitors; (b) insulin sensitizers selected from the group consisting of (i) PPAR agonists and (ii) biguanides; (c) insulin and insulin analogs mimetics; (d) sulfonylureas and other insulin secretagogues; (e) α-glucosidase inhibitors; (f) glucagon receptor antagonists; (g) GLP-1, GLP-1 analogs and mimetics, and GLP-1 receptor agonists; (h) GIP, GIP analogs and mimetics, and GIP receptor agonists; (i) PACAP, PACAP analogs and mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA: cholesterol acyltransferase inhibitors, and (viii) anti-oxidants; (k) PPARδ agonists; (l) antiobesity compounds; (m) an ileal bile acid transporter inhibitor; (n) anti-inflammatory agents excluding glucocorticoids; and (o) protein tyrosine phosphatase-1B (PTP-1B) inhibitors.

In another embodiment, the present invention provides a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment, said method comprising administering to the patient a therapeutically effective amount of a pharmaceutical composition of the 2S,4R ketoconazole enantiomer substantially free of the 2R,4S enantiomer and an HMG-CoA reductase inhibitor. In one embodiment, the HMG-CoA reductase inhibitor is a statin. In one embodiment, the statin is selected from the group consisting of lovastatin, simvastatin, pravastatin, fluvastatin, atorvastatin, itavastatin, ZD-4522, rosuvastatin, and rivastatin.

In another embodiment, the present invention provides a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a pharmaceutical composition of the 2S,4R ketoconazole enantiomer substantially free of the 2R,4S enantiomer and an HMG-CoA reductase inhibitor. In another embodiment, the method for delaying the onset or reducing the risk of developing atherosclerosis in a human patient in need of such treatment further comprises the administration of a cholesterol absorption inhibitor in combination with a statin HMG-CoA reductase inhibitor and a pharmaceutical composition of the 2S,4R ketoconazole enantiomer substantially free of the 2R,4S enantiomer. In one embodiment, the cholesterol absorption inhibitor is a cholesterol transfer ester protein (CTBP) inhibitor. In another embodiment the CTEP inhibitor is ezetimibe.

In another embodiment, the invention provides a method for delaying the onset or reducing the risk of developing atherosclerosis in a human patient in need of such treatment, said method comprising administering to said patient an effective amount of a pharmaceutical composition of the 2S,4R ketoconazole enantiomer substantially free of the 2R,4S enantiomer and an HMG-CoA reductase inhibitor. In one embodiment, the HMG-CoA reductase inhibitor is a statin. In one embodiment, the statin is selected from the group consisting of: lovastatin, simvastatin, pravastatin, fluvastatin, atorvastatin, itavastatin, ZD-4522, rosuvastatin and rivastatin. In one embodiment, the statin is simvastatin.

The invention, numerous embodiments of which have been described above, may be further appreciated and understood by the examples below, which demonstrate that the 2S,4R enantiomer is more effective than racemic ketoconazole or the 2R,4S enantiomer in the racemate at reducing the concentration of the active glucocorticoid in the plasma and does not impair (or impairs to a significantly less extent) drug metabolism as does racemic ketoconazole.

EXAMPLES

Example 1: Measurement of Corticosterone and Cholesterol Following Dosing with Racemic Ketoconazole and the Enantiomers of Ketoconazole The effect of ketoconazole and the ketoconazole enantiomers on corticosterone levels in the plasma of Sprague Dawley rats was determined. For the experiment described in FIG. 1, the four enantiomers and the racemic ketoconazole were suspended in olive oil. To generate the results shown in FIG. 1, five groups (eight per group) of rats were used. The rats were maintained on a 14/10 hour light/dark cycle and allowed free access to food and water. Each rat was dosed (200 mg drug/kg body weight) via a gastric tube. The rats in group 1 were dosed with the vehicle (olive oil), while the rats in the other four groups were dosed with one of the four ketoconazole enantiomers as indicated. All of the rats were dosed between 2.00 and 3.00 pm and were sacrificed four hours later (between 6.00 and 7.00 pm). Plasma was prepared and the concentration of corticosterone determined by an enzyme linked immuno assay (ELISA). In rats, the predominant active glucocorticoid is corticosterone; in humans, the predominant active glucocorticoid is the closely related molecule cortisol. The results shown in FIG. 1 demonstrate that, in comparison to the vehicle control, the two trans enantiomers (2S4S and 2R4R), when given to rats at 200 mg/kg, have little effect on the blood level of corticosterone. In contrast, both cis enantiomers reduce corticosterone, with the 2S,4R being significantly more efficacious than 2R,4S.

Figure 2:
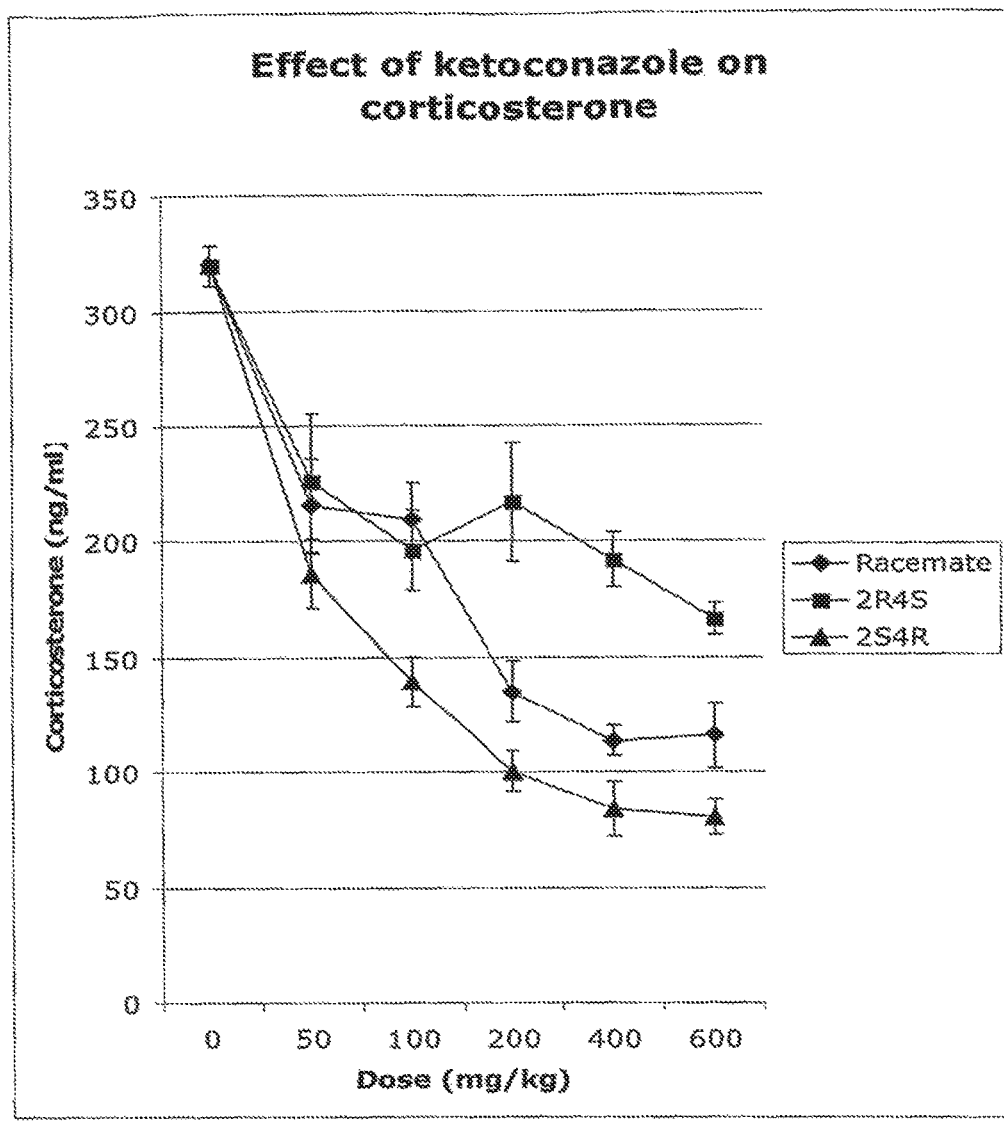
FIG. 2 shows the effect of racemic ketoconazole and of the two cis enantiomers 2R,4S and 2S,4R on plasma corticosterone. The 2S,4R enantiomer is more effective at lowering corticosterone than either racemic ketoconazole or the other enantiomer present in racemic ketoconazole (2R,4S). The concentration of corticosterone in the plasma of Sprague-Dawley rats was determined four hours after delivery by oral gavage of the indicated amount of either racemic ketoconazole or the two enantiomers (2S,4R and 2R,4S) present in racemic ketoconazole.

For the experiment summarized in FIG. 2, there was one vehicle (olive oil) group of 9 rats, and 15 groups of 10 rats/group treated with the specified dose of ketoconazole or one of the two (2S,4R and 2R,4S) cis enantiomers of ketoconazole. The rats were maintained and dosed as described above. Plasma was prepared and the concentration of corticosterone in the plasma determined by ELISA. The results shown in FIG. 2 demonstrate that there is a dose dependent effect of both ketoconazole and the enantiomers on corticosterone levels and that the 2S,4R enantiomer is significantly more efficacious than both the ketoconazole racemate and the other cis enantiomer (2R,4S).

Figure 3:
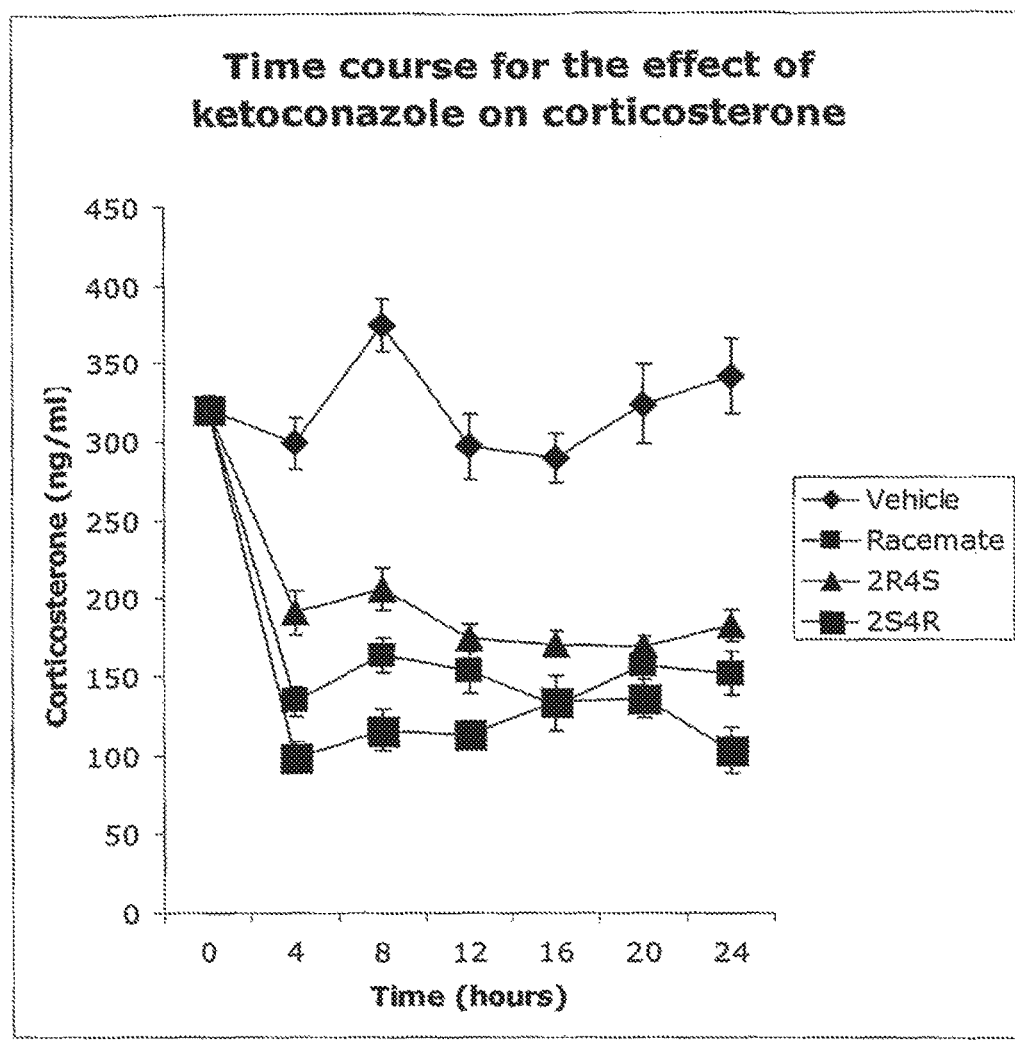
FIG. 3 shows the effect of racemic ketoconazole or the two enantiomers 2R,4S and 2S,4R on the time course of depression of plasma corticosterone. The 2S,4R enantiomer is more effective at lowering corticosterone than either racemic ketoconazole or the other cis enantiomer present in racemic ketoconazole (2R,4S). The concentration of corticosterone in the plasma of Sprague-Dawley rats was determined at the indicated time after delivery by oral gavage of 200 mg/kg of either racemic ketoconazole or the two enantiomers (2S,4R and 2R,4S) present in racemic ketoconazole.

For the experiment summarized in FIG. 3 and FIG. 8, there were six groups of ten rats/group that were treated with the vehicle (olive oil) and eighteen groups of 10 rats/group treated with either ketoconazole or one of the two (2S,4R and 2R,4S) cis enantiomers of ketoconazole. The rats were maintained as described above; the drugs were suspended in olive oil, and each rat was dosed once via gastric tube to achieve a dose of 200 mg/kg. All of the rats were dosed at a specific time so that all terminations occurred between 6 and 7 pm. For example, the rats treated for 24 hours were dosed between 6 and 7 pm the day prior to sacrifice, and the rats treated for 12 hours were dosed between 6 and 7 am on the day of sacrifice. Following sacrifice, plasma was prepared, and the concentration of corticosterone in the plasma was determined by ELISA. In the same plasma samples, total cholesterol levels were also determined. The results shown in FIG. 3 demonstrate that the 2S,4R is significantly more efficacious than the 2R,4S enantiomer at lowering corticosterone and that this increased efficacy persists for at least 24 hours. The efficacy of the racemate is intermediate between the two enantiomers. Similarly, the results shown in the table below demonstrate that the 2S,4R is significantly more efficacious than the 2R,4S enantiomer at lowering cholesterol. The results show that efficacy of the racemate is intermediate between the two enantiomers.

Effect of Racemic Ketoconazole and the 2S,4R, and 2R,4S Enantiomers on Cholesterol Levels in Rats at the Indicated Time after Oral Dosing with 200 mg of the Indicated Drug (or Vehicle)

| Time (hours) | Cholesterol Levels (mean ± SEM; mg/dL) | | | |
|---|---|---|---|---|
| | Vehicle | 2S,4R (DIO-902) | 2R,4S | Racemate |
| 4 | 77.3 ± 3.9 | 69.6 ± 1.9 | 85.1 ± 7 | 81.2 ± 3.9 |
| 8 | 73.5 ± .5 | 73.5 ± 3.1 | 85.1 ± 5.4 | 73.5 ± 2.3 |
| 12 | 69.6 ± 3.5 | 77.3 ± 3.9 | 77.3 ± 1.9 | 69.6 ± 2.3 |
| 16 | 69.6 ± 1.9 | 61.9 ± 3.1 | 77.3 ± 4.6 | 69.6 ± 3.1 |
| 20 | 69.6 ± 1.9 | 58 ± 1.2 | 69.6 ± 2.7 | 65.7 ± 2.7 |
| 24 | 65.7 ± 2.7 | 61.9 ± 3.1 | 69.6 ± 1.5 | 65.7 ± 3.9 |

Example 2: Measurement of Drug Exposure Following Dosing with Racemic Ketoconazole and the Cis Enantiomers of Ketoconazole In this example, dogs were treated with ketoconazole or with the 2S,4R enantiomer only, and the plasma levels of the corresponding drug were determined.

Pharmacokinetics of Racemic Ketoconazole

Two groups of three male and three female dogs per group were studied. Each dog was dosed with racemic ketoconazole, and the concentration of racemic ketoconazole in the plasma of the dogs was determined on the first day of dosing and again after four weeks of daily dosing. The two groups differed in that, in one group, the racemic ketoconazole was provided as a dry white powder in a gelatin capsule, and in the other, the racemic ketoconazole was provided as a suspension in olive oil.

The dogs were purpose bred beagle dogs obtained from Covance Research Products, Inc., Cumberland, Va. USA. The dogs were 4.5 to 5 months old at the start of dosing. The dogs were housed in suspended, stainless steel cages. Air conditioning provided a minimum of 10 air changes/hour. The temperature and relative humidity ranges were 18 to 29 degree Centigrade and 30% to 70%, respectively. With a few exceptions when manual over-ride was used for study related activities, fluorescent lighting was controlled automatically to give a cycle of 12 hours light (0700-1900) and 12 hours dark. Certified canine diet (#8727C, Harlan Teklad) was available ad libitum. Water was provided ad libitum via an automatic watering system. After arrival at the test lab, the dogs were acclimated for 19 days and then randomized, as needed, to a treatment group using a computerized blocking procedure designed to achieve body weight balance. After allocation, the mean body weights were calculated and inspected to ensure there were no unacceptable differences between groups. The animals were individually identified by means of an electronic implant.

In the first group, the dogs were dosed daily by oral delivery of a gelatin capsule (size 13, Torpac, New Jersey, USA). The capsule contained sufficient racemic ketoconazole to provide a dose of 40 mg drug/kg body weight/day. The capsules were prepared weekly for each animal based on individual body weights. The capsules and the bulk drug were stored at room temperature in sealed containers. For the second group, the gelatin capsules contained sufficient racemic ketoconazole suspended in olive oil to provide a dose of 40 mg drug/kg body weight/day. The animals were observed approximately 1 to 2 hours after dosing, daily, throughout the experiment. Blood samples (1 ml into lithium heparin) were taken from the jugular vein from each of the animals on the first day of dosing and again at week 4 (after 28 daily doses) at 0 (pre-dose) 1, 2, 4, 8, 12, and 24 hours after dosing. At week 4, the pre-dose sample was timed to be 24 hours post-dosing on the previous day. Plasma samples were stored frozen at −70 degrees Centigrade until analysis. The plasma samples were analyzed for racemic ketoconazole as described below using racemic ketoconazole as a standard.

Figure 4:
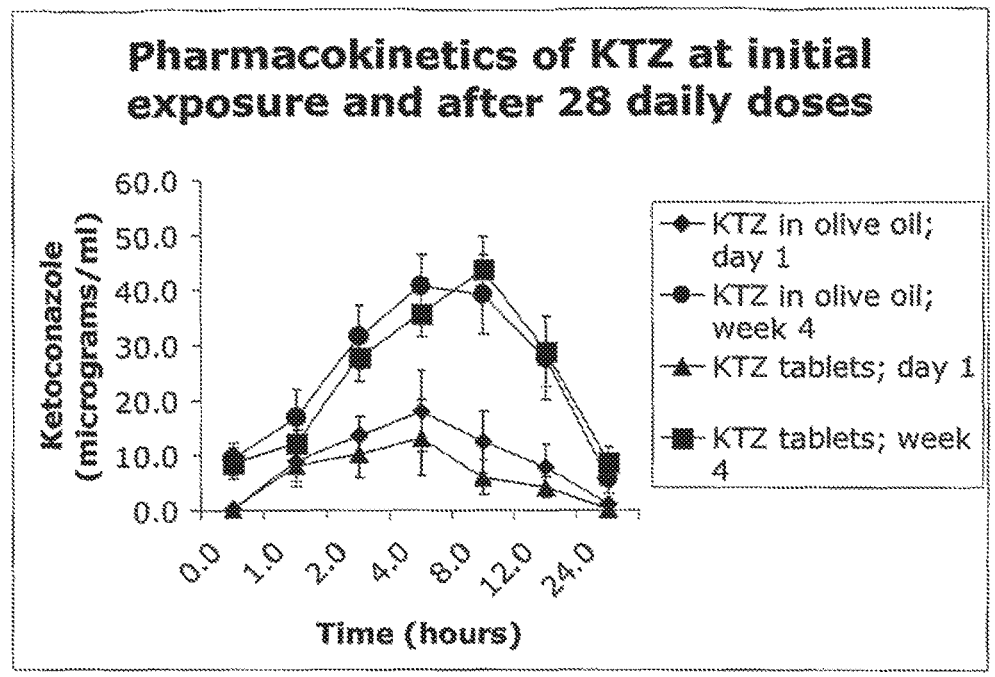
FIG. 4 shows the effect of prior exposure to ketoconazole on the pharmacokinetic profile of racemic ketoconazole in dogs. The pharmacokinetic profile of racemic ketoconazole is clearly altered by prior exposure to racemic ketoconazole. The concentration of racemic ketoconazole in the plasma of dogs that were dosed with racemic ketoconazole daily for 28 days (in two different forms: in suspension in olive oil and in a solid tablet form) is significantly greater than the concentration of racemic ketoconazole in the plasma of dogs that were treated only once.
Figure 5:
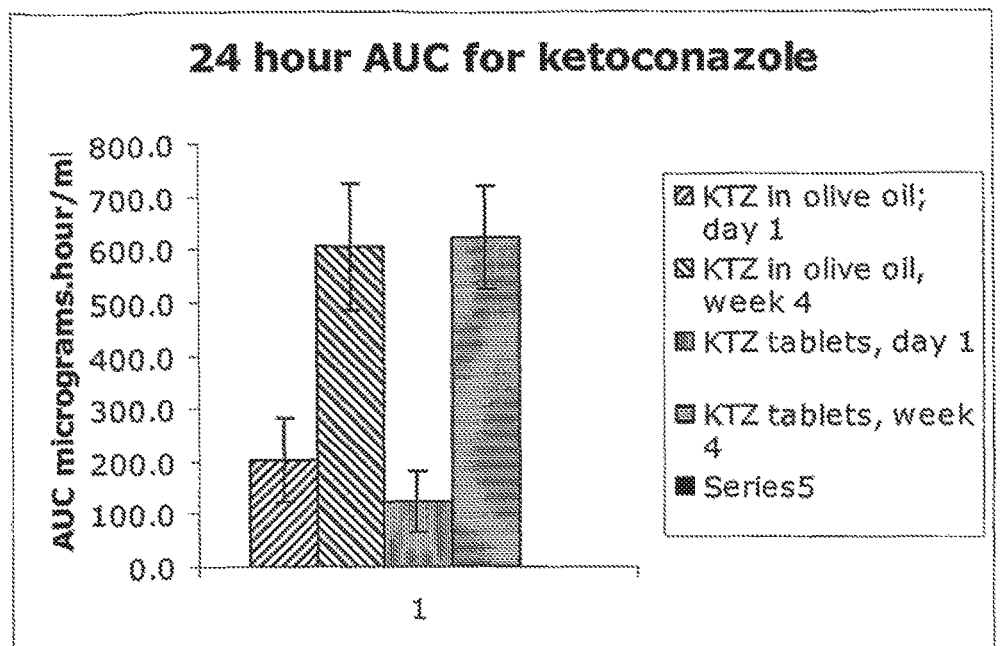
FIG. 5 shows the effect of prior exposure to racemic ketoconazole on the pharmacokinetic profile of racemic ketoconazole in dogs. The Area Under the Curve (AUC) of racemic ketoconazole is increased by prior exposure to racemic ketoconazole. The AUC of the pharmacokinetic profile shown in FIG. 4 was calculated according to the trapezoid rule. The AUC of racemic ketoconazole is greater in dogs treated daily for 28 days as compared to dogs treated only once. The increase in AUC is independent of the form in which the racemic ketoconazole was administered.

As shown in FIG. 4, the pharmacokinetic profile (concentration as a function of time) of racemic ketoconazole in the plasma of the dogs dosed only once (and the plasma assayed over the first 24 hours after dosing) was significantly diminished as compared to the pharmacokinetic profile of racemic ketoconazole in the plasma of dogs dosed daily for 28 days (and the plasma assayed over the 24 hours after the last of the 28 doses). This effect was obtained in both groups (racemic ketoconazole administered as a dry powder and racemic ketoconazole administered as a suspension in olive oil). The Area Under the Curve (AUC) was calculated using the linear trapezoidal rule. The AUC determined after a single dose was significantly reduced in comparison to the AUC determined after 28 daily doses (see FIG. 5). Again, this effect was seen in both groups (racemic ketoconazole administered as a dry powder and racemic ketoconazole administered as a suspension in olive oil).

Pharmacokinetics of the 2S,4R Enantiomer

Another group of three female and three male dogs was dosed with the 2S,4R enantiomer of ketoconazole, and the concentration of the enantiomer in the plasma of the dogs was determined on the first day of dosing and again after four weeks of daily dosing.

The dogs were purpose bred beagle dogs obtained from Harlan, Bicester, Kent, England. The dogs were 4.5 to 5 months old and weighed between 6.7 and 8.85 kg on arrival at the test lab. They were approximately 6 to 6.5 months of age at the start of dosing. The dogs were housed in a single exclusive room, air conditioned to provide a minimum of 10 air changes/hour. The temperature and relative humidity ranges were 16 to 24 degree Centigrade and 30% to 80%, respectively. With a few exceptions when manual over-ride was used for study related activities, fluorescent lighting was controlled automatically to give a cycle of 12 hours light (0700-1900) and 12 hours dark. The animals were housed singly during the day in pens of 2.25 m², and animals of the same experimental group and sex were housed overnight in pens of at least 4.5 m².

Each animal was offered 400 g of Harlan Teklad Dog Maintenance Diet (Harlan, Teklad, Bicester, England) and a Winalot Shapes biscuit (Friskies Pet Care, Suffolk, England) each morning after dosing with ketoconazole or the 2 S4R enantiomer. Water was provided ad libitum via an automatic watering system. Bedding was provided on a daily basis to each animal by use of clean wood flakes/shavings (Datesand Ltd. Manchester, England). After arrival at the test lab, the dogs were acclimated for 7 weeks and then randomized, as needed, to a treatment group based on a stratified randomization procedure, using littermate data and the most recent body weight data. After allocation, the mean body weights were calculated and inspected to ensure there were no unacceptable differences between groups. The animals were individually identified by means of an electronic implant.

Three male and three female dogs were dosed daily by oral delivery of a gelatin capsule (size 13, Torpac, New Jersey, USA). The capsule contained sufficient 2S,4R enantiomer to provide a dose of 20 mg drug/kg body weight/day. The capsules were prepared weekly for each animal based on individual body weights. The capsules and the bulk drug were stored at room temperature in sealed containers. The animals were observed approximately 1 to 2 hours after dosing, daily throughout the experiment. Blood samples (1 ml into lithium heparin) were taken from the jugular vein from each of the animals on the first day of dosing and again at week 4 (after 28 daily doses) at 0 (pre-dose) 1, 2, 4, 8, and 24 hours after dosing. At weak 4, the pre-dose sample was timed to be 24 hours post-dosing on the previous day. Plasma samples were stored frozen at −70 degrees Centigrade until analysis. The plasma samples were analyzed for the 2S,4R enantiomer as described below using racemic ketoconazole as a standard.

Figure 6:
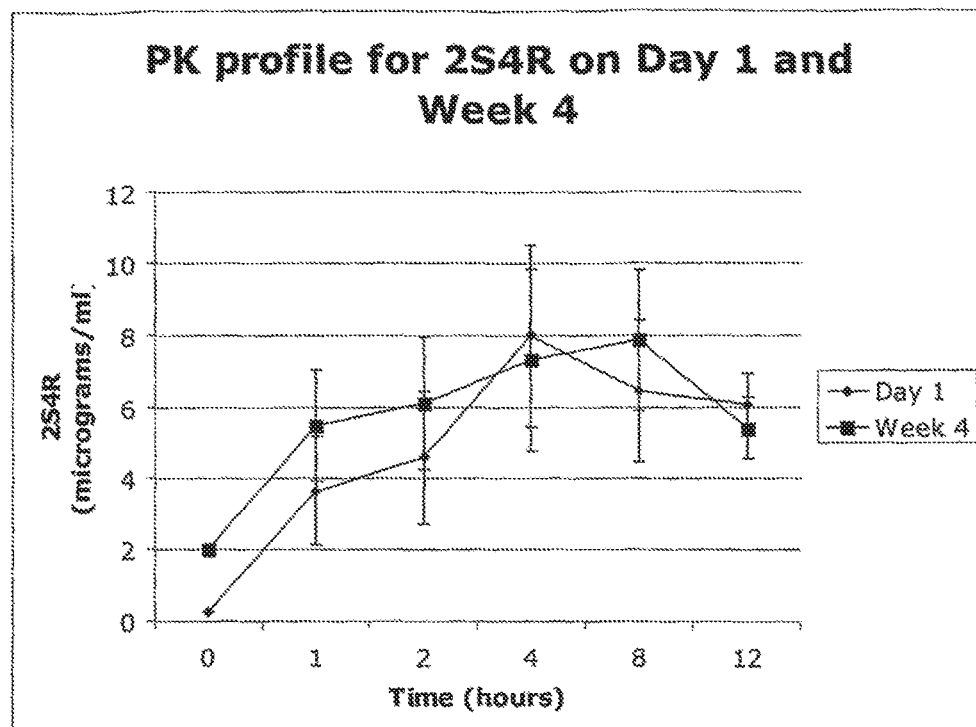
FIG. 6 shows the effect of prior exposure to the 2S,4R enantiomer of ketoconazole on the pharmacokinetic profile of the 2S,4R enantiomer of ketoconazole in dogs. The pharmacokinetic profile of the 2S,4R enantiomer of ketoconazole is not altered by prior exposure to the 2S,4R enantiomer of ketoconazole. The concentration of the 2S,4R enantiomer of ketoconazole in the plasma of dogs that were dosed either once with the 2S,4R enantiomer or were dosed daily for 28 days is not increased in the dogs treated for 28 days as compared to dogs treated only once.
Figure 7:
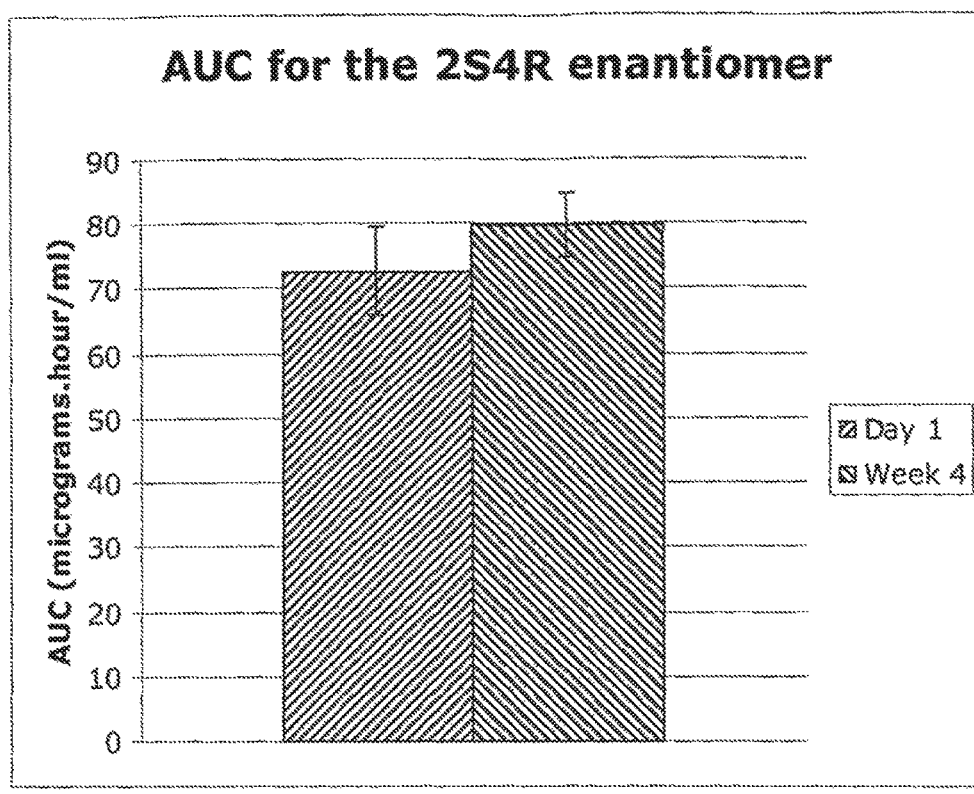
FIG. 7 shows the effect of prior exposure to the 2S,4R enantiomer of ketoconazole on the AUC of the 2S,4R enantiomer of ketoconazole in dogs. The AUC of 2S,4R enantiomer of ketoconazole is not increased by prior exposure to the 2S,4R enantiomer of ketoconazole. The AUC of the 2S,4R enantiomer of ketoconazole is the same in dogs treated daily for 28 days as compared to dogs treated only once.

As shown in FIG. 6, the pharmacokinetic profile (concentration as a function of time) of the 2S,4R enantiomer in the plasma of the dogs dosed only once (and the plasma assayed over the first 24 hours after dosing) was not distinguishable from the pharmacokinetic profile of the 2S,4R enantiomer in the plasma of dogs dosed daily for 28 days (and the plasma assayed over the 24 hours after the last of the 28 doses). The Area Under the Curve (AUC) was calculated using the linear trapezoidal rule. The AUC determined after a single dose was not distinguishable from the AUC determined after 28 daily doses (see FIG. 7).

Ketoconazole Assay Procedures

Assays were established and validated using racemic ketoconazole. Plasma from the dogs treated with racemic ketoconazole, the 2S,4R enantiomer, or the vehicle control was prepared by standard methods and frozen at −70 degrees Centigrade until assayed. To assay the concentration of racemic ketoconazole (or the 2S,4R enantiomer), the plasma samples were thawed and briefly vortexed, and 100 microliter aliquots taken. An internal standard (clotrimazole 25 microliters, 100 micrograms/mL, Sigma Aldrich) was added to the samples and mixed briefly. The samples were subjected to solid phase extraction using OASIS HLB (Waters Ltd. 730-740 Centennial Court, Centennial Park, Elstree, Hertsfordshire WD6 3SZ England). The eluates were evaporated to dryness under a stream of nitrogen at nominal 40 degrees Centigrade and the residues re-dissolved in a mobile phase prior to analysis by liquid chromatography with ultraviolet light detection.

Concentrations of racemic ketoconazole and ketoconazole 2S,4R enantiomer in calibration standards and study samples were determined using least squares regression with reciprocal of the concentration (1/x) as weighting to improve accuracy at low levels. The lower limit of quantification (LLOQ) for ketoconazole in dog plasma was 0.25 micrograms/milliliter with linearity demonstrable to 25 micrograms/milliliter. The coefficients of determination ($r^2$) were better than or equal to 0.99226.

Example 3: Formulation and Clinical Trial of the 2S,4R Enantiomer Substantially Free of the 2R,4S Enantiomer of Ketoconazole in Type 2 Diabetes A. Abbreviations The following abbreviations are used in this Example.

| Term/Abbreviation | Explanation |
| --- | --- |
| ALT | alanine transaminase |
| AST | aspartate transaminase |
| AUC | area under the curve |
| Bid | twice daily |
| Biw | twice weekly |
| BUN | blood urea nitrogen |
| CV | coefficient of variation |
| ELISA | enzyme-linked immunosorbent assay |
| FDA | Food and Drug Administration |
| GI | Gastrointestinal |
| GLP | Good Laboratory Practice |
| IND | Investigational New Drug (application) |
| IV | Intravenous |
| MedDRA | *Medical Dictionary for Regulatory Activities* |
| NDA | New Drug Application |

-continued

| Term/Abbreviation | Explanation |
|---|---|
| NOAEL | no-observered-adverse-effect level |
| PBS | phosphate-buffered saline |
| Qd | Daily |
| Qw | Weekly |
| RP-HPLC | reverse-phase high performance liquid chromatography |
| SBA | Summary Basis of Approval |
| SC | subcutaneous, subcutaneously |
| SD | standard deviation |
| SDS-PAGE | sodium dodecyl sulfate-polyacrylamide gel electrophoresis |
| SE-HPLC | size-exclusion high-performance liquid chromatography |
| USP | United States Pharmacopoeia |
| WBC | white blood cell |

B. Overview

An illustrative formulation of the 2S,4R enantiomer of ketoconazole substantially free of the 2R,4S enantiomer (hereinafter called DIO-902) is described in this Example together with pre-clinical data supporting its testing as an investigational new drug in human clinical trials for the treatment of the hyperglycemia associated with type 2 diabetes mellitus. All references cited herein are incorporated herein by reference. Secondary benefits of this drug candidate are expected to include reduced total and LDL cholesterol, reduced blood pressure and reduced visceral adiposity. Racemic ketoconazole (the mixture of the two enantiomers 2S,4R and 2R,4S) is an approved drug (NIZORAL®) for the treatment of a variety of fungal infections. As racemic ketoconazole also inhibits cortisol synthesis, this drug is used as a non-approved therapy for patients with Cushing's syndrome. In these patients racemic ketoconazole reduces glucose, cholesterol, and blood pressure. As cortisol may be a contributing causal factor in the development of type 2 diabetes, clinical trials with racemic ketoconazole have been carried out in these patients. The results of these clinical trials support treating type 2 diabetes through lowering of plasma cortisol. Racemic ketoconazole has, however, been associated with hepatotoxicity. Preclinical results support that DIO-902 may be safer and more efficacious than the racemic mixture.

DIO-902 is the 2S,4R enantiomer of ketoconazole (2S,4R cis-1-acetyl-4-[4-[[2-(2,4-dichlorophenyl)-2-(1H-imidazol-1-ylmethyl)-1,3-dioxolan-4-yl]methoxy]phenyl]piperazine). Ketoconazole, an approved drug, is a racemic mixture of both the 2S,4R enantiomer and the 2R,4S enantiomer. DIO-902 has been purified from the racemic mixture and is largely (greater than 99%) free of the 2R,4S enantiomer. It is anticipated that the primary pharmacological effect of DIO-902 will be through the suppression of cortisol synthesis, with secondary benefits exerted through a reduction in cholesterol synthesis. DIO-902 has been formulated into immediate release tablets. The toxicology of DIO-902 has been tested in dogs. At oral doses of up to 20 mg/kg/day for 28 days the only noted effect was a reduction in food intake and a reduction in body weight and a trend to a decrease in cholesterol. There were no noted changes in any of the other serum chemistry or the hematological parameters measured. Higher single doses have been used in rats. At 200 mg drug/kg body weight DIO-902 suppresses testosterone to 10% of basal. The suppression occurs within four hours of dosing and testosterone levels return to normal within 8 hours. DIO-902 is orally available and reaches a maximal plasma concentration between 2 and 8 hours in dogs. DIO-902 at 200 mg drug/kg body weight reduces serum levels of the active glucocorticoid in rodents (corticosterone) to 25% of basal within 4 hours of oral dosing. This dose of drug also suppresses plasma cholesterol. Thus, DIO-902 (2S,4R) is significantly more potent with respect to reducing corticosterone in rats than is the other enantiomer (2R,4S) and is more potent with respect to reducing cholesterol in rats than is the other enantiomer.

DIO-902 has not been previously administered as a single chemical entity to human patients. However, this molecule has been widely administered as part of the approved racemic mixture. When normal volunteers are given the racemic mixture, both enantiomers are orally available, and, after a 200 mg dose, a maximum plasma concentration of the DIO-902 (approximately 3.6 µg/mL) is reached at 2 hours. The approved use for the racemic mixture is for the treatment of fungal infections and the approved dose is 200 mg BID. In addition, higher doses of the racemic mixture (up to 2000 mg/day) have been used. The racemic mixture has also been used for non-approved indications, including Cushing's syndrome and prostate cancer. The racemic mixture can cause hepatoxicity and reduces testosterone, and 1,25 dihydroxy Vitamin D.

The diagnostic criterion for type 2 diabetes is hyperglycemia. Specifically, the American Diabetes Association recognizes a diagnosis of diabetes in which the patient displays one of the following three characteristics: a) a casual (any time of day or night) plasma glucose value of greater than 200 mg/dL (11.1 mmol/L) on two separate occasions in presence or absence of the symptoms of diabetes (polyuria, polydipsia or unexplained weight loss), or b) a fasting (8 hour) plasma glucose value of greater than 126 mg/dl (7 mmol/L), or c) a plasma glucose value of greater than 200 mg/dl (11.1 mmol/L) 2 hours after a 75 gram oral load of glucose. Prospective studies have convincingly demonstrated that hyperglycemia is causally associated with long term microvascular complications including nephropathy and retinopathy. In addition to the diagnostic hyperglycemia, patients with type 2 diabetes have an increased incidence of hypertension, hypertriglyceridemia and hypercholesterolemia. These significantly increase the risk of macrovascular and microvascular diseases.

The most important acquired risk factor for the development of type 2 diabetes is adiposity, more specifically, visceral adiposity. There are also genetic susceptibilities. Except for a small number of clearly defined syndromes such as Maturity Onset Diabetes of the Young (MODY, principally caused by mutations in the gene encoding glucokinase) most of the genes that contribute to the development of type 2 diabetes have not been identified. Physiologically, hyperglycemia in patients with type 2 diabetes is caused primarily by insulin resistance—a relative failure of insulin to stimulate glucose uptake and to suppress glucose production. This insulin resistance is initially partially compensated for by increased insulin synthesis. In many patients there is a later stage where insulin production declines with a significant worsening of the hyperglycemia. There is still some uncertainty surrounding the cause of the insulin resistance with evidence supporting key roles for intracellular lipids and direct alterations in the activity of insulin signaling molecules. Increased glucocorticoid bioactivity could also be a direct or indirect cause of insulin resistance and beta cell failure.

An important treatment option in patients with type 2 diabetes is dietary modification, increased exercise and weight loss. Unfortunately, while effective, this option has proved difficult to implement. Pharmacological therapeutics include metformin, sulphonylureas (and Meglitinide and Nateglinide which, like the sulphonylureas increase insulin secretion), the glitizides (Pioglitizone and Rosiglitizone) and insulin. Although effective, glucose control remains suboptimal. In 2005, at their annual conference, The American Association of Clinical Endocrinologists (AACE) announced a new glycosylated hemoglobin standard of 6.5% or lower for patients with type 2 diabetes. This new standard is part of an effort to prevent diabetes complications. Dr. Paul Jellinger, current president of the American College of Endocrinology (ACE), said that the AACE is embarking on this effort after a study showed two thirds of Americans with type 2 diabetes are not adequately treating the disease. Further, none of the drugs approved for glucose control appear to target the underlying cause(s) of the insulin resistance and some (such as insulin and the glitizones) can cause weight gain, which may exacerbate the insulin resistance. One advantage of DIO-902 over currently available therapeutics is that this drug is believed to targets one of the causes of type 2 diabetes.

An additional potential advantage of DIO-902 is the possibility that this drug is believed to be able to improve significantly other cardiovascular risk factors including hypercholesterolemia and hypertension. The majority of patients with type 2 diabetes have coexisting cardiovascular risk factors, including hypertension, dyslipidemia, and microalbuminuria (Alexander et al. (2003). "NCEP-defined metabolic syndrome, diabetes, and prevalence of coronary heart disease among NHANES III participants age 50 years and older." *Diabetes* 52(5): 1210-4). Independent of glycemic control, controlling hypertension and microalbuminuria has been shown to prevent both the micro- and macrovascular complications of diabetes. Further, the control of dyslipidemia contributes to cardiovascular risk reduction and may decrease the risk of developing diabetic nephropathy (Bell (2002). "Chronic complications of diabetes." *South Med J* 95(1): 30-4). Racemic ketoconazole reduces blood pressure and cholesterol in patients with Cushing's syndrome (Sonino et al. (1991). "Ketoconazole treatment in Cushing's syndrome: experience in 34 patients." *Clin Endocrinol (Oxf)* 35(4): 347-52) and reduces cholesterol in patients with hypercholesterolemia (Gylling et al. (1993). "Effects of ketoconazole on cholesterol precursors and low density lipoprotein kinetics in hypercholesterolemia." *J Lipid Res* 34(1): 59-67) and prostate cancer (Miettinen (1988). "Cholesterol metabolism during ketoconazole treatment in man." *J Lipid Res* 29(1): 43-51). Data obtained in the Phase 2 clinical trial described by IND 60,874 also support that racemic ketoconazole reduces total and LDL cholesterol and blood pressure in patients with type 2 diabetes. Preclinical results described here and in Example 1 indicate that DIO-902 will have enhanced activities with respect to blood pressure and cholesterol.

As noted above, the behavioral and therapeutic options available for patients with type 2 diabetes are inadequate. The life style changes have proved very difficult to implement. The therapeutic options do not target the underlying cause(s) of the disease and some therapies, for example insulin and the glitizones, may exacerbate factors such as body weight that contribute to the underlying insulin resistance. Further, most therapeutic options reduce one (hyperglycemia), or at most two (hyperglycemia and either of hypertension or dyslipidemia) of the factors that contribute to the micro and macro vascular complications. DIO-902 is believed to target an important causal component of type 2 diabetes (elevated cortisol bioactivity) and to be able to treat the hyperglycemia, hypertension and dyslipidemia in these patients.

That glucocorticoids can decrease insulin sensitivity and increase plasma glucose levels through effects on the liver, fat, muscle and pancreatic beta cells in humans (as well as in experimental animals) is well established (McMahon et al. (1988). "Effects of glucocorticoids on carbohydrate metabolism." *Diabetes Metab Rev* 4(1): 17-30). In rodent models, glucocorticoids are necessary for the development of obesity, glucose intolerance and diabetes and, in some cases increased glucocorticoid activity is sufficient to cause diabetes. In humans, pathological increases in glucocorticoid levels (as seen in patients with Cushing's syndrome) can also cause diabetes. More recently there is a growing recognition that patients with incidental adrenal tumors (incidentalomas) and more subtle increases in cortisol activity are at significantly elevated risk for developing diabetes, glucose intolerance hypertension, diffuse obesity and dyslipidemia (Terzolo et al. (1998). "Subclinical Cushing's syndrome in adrenal incidentaloma." *Clin Endocrinol (Oxf)* 48(1): 89-97; Rossi et al. (2000). "Subclinical Cushing's syndrome in patients with adrenal incidentaloma: clinical and biochemical features." *J Clin Endocrinol Metab* 85(4): 1440-8).

There are multiple reports suggesting that patients with type 2 diabetes have increased levels of plasma cortisol particularly in the period between the nadir in the diurnal rhythm that occurs around midnight and the early morning rise in cortisol. Cameron (Cameron et al. (1987). "Hypercortisolism in diabetes mellitus." *Diabetes Care* 10(5): 662-4) reported that while the 24-hour cortisol levels were greater at all time points in patients with diabetes than non-diabetics, the largest difference was at 8 am. This study also examined cortisol levels in diabetic patients following a dexamethasone suppression test Following ingestion of 1 mg dexametbasone, cortisol levels remained significantly elevated in the early morning in the diabetic patients but not in the controls. Similarly, night time (Lentle and Thomas (1964). "Adrenal Function And The Complications Of Diabetes Mellitus." *Lancet* 14: 544-9; Vakov (1984). "English translation of Circadian rhythm of cortisol secretion in diabetes mellitus patients.") and early morning (Lee et al. (1999). "Plasma insulin, growth hormone, cortisol, and central obesity among young Chinese type 2 diabetic patients." *Diabetes Care* 22(9): 1450-7) cortisol levels were higher in patients with type 2 diabetes than controls.

As cortisol will increase blood pressure and plasma glucose, the relationship between these parameters and cortisol in patients with type 2 diabetes has been studied. One study reported that, in patients with type 2 diabetes, there is a greater disturbance of the cortisol diurnal rhythm in those patients with hypertension compared to normotensive diabetics (Kostic and Secen (1997). "Circadian rhythm of blood pressure and daily hormonal variations" *Mod Pregl* 50(1-2): 37-40). One study reported that maturity onset, slightly overweight, non-insulin requiring diabetic patients had higher cortisol levels than non-diabetics and that diabetic patients had a clear diurnal glucose rhythm and their peak glucose coincided with the peak cortisol (Faiman and Moorhouse (1967). "Diurnal variation in the levels of glucose and related substances in healthy and diabetic subjects during starvation." *Clin Sci* 32(1): 111-26). Similarly, another study reported a strong correlation (r=0.82; p<0.01) between cortisol and glucose concentrations at 8:00 am in patients with type 2 diabetes (Atiea et al. (1992). "The dawn phenomenon and diabetes control in treated NIDDM and IDDM patients." *Diabetes Res Clin Pract* 16(3): 183-90). One study found an increase in the 6 am cortisol levels in relatively lean type 2 diabetic patients and a correlation (r=0.55; p<0.05) between plasma cortisol and the rate of glucose production as measured by tracer dilution (Richardson and Tayek (2002). "Type 2 diabetic patients may have a mild form of an injury response: a clinical research center study." *Am J Physiol Endocrinol Metab* 282(6): E1286-90).

Adrenocorticotrophic hormone (ACTH, the pituitary hormone that regulates adrenal corticosteroid production) has also been measured in a smaller number of studies. One study examined cortisol and ACTH in normal volunteers and in diabetes patients with and without autonomic neuropathy (AN). The diabetes patients with AN had higher HbA1c levels than the diabetic patients without AN and also had higher ACTH and cortisol levels than both the patients without AN and the controls (Tsigos et al. (1993). "Diabetic neuropathy is associated with increased activity of the hypothalamic-pituitary-adrenal axis." *J Clin Endocrinol Metab* 76(3): 554-8). The increase in ACTH in the patients with diabetes and AN compared to the controls did not reach statistical significance. One study reported that ACTH was elevated in patients with type 2 (but not type 1) diabetes (Varmes et al. (1985). "Increased plasma levels of immunoreactive beta-endorphin and corticotropin in non-insulin-dependent diabetes." *Lancet* 2(8457): 725-6).

In contrast to these predominantly positive correlative data, another study (Serio et al. (1968). "Plasma cortisol response to insulin and circadian rhythm in diabetic subjects." *Diabetes* 17(3): 124-6) reported normal plasma levels of cortisol in patients diabetes. These patients had quite mild diabetes as their glucose was controlled solely by diet. Similarly another study (with a smaller number of individuals) did not find an increase in levels of circulating cortisol in patients with type 2 diabetes (Kerstens et al. (2000). "Lack of relationship between 11beta-hydroxysteroid dehydrogenase setpoint and insulin sensitivity in the basal state and after 24 h of insulin infusion in healthy subjects and type 2 diabetic patients." *Clin Endocrinol (Oxf)* 52(4): 403-11).

Pharmacological intervention to reduce plasma cortisol has proved effective in treating diabetes, hypertension and dyslipidemia in patients with Cushing's syndrome. Sonino reported on 34 patients with Cushing's syndrome who had their hypercortisolemia reduced by ketoconazole at doses between 400 and 800 mg/day (Sonino et al. 1991 supra). Three patients that were hyperglycemic but not on any diabetes medications became euglycemic; of three other hyperglycemic patients that were on diabetes medications, one was able to discontinue the drug and the other two were able to reduce use of their hypoglycemic medications. Similar results have been reported by Winquist (Winquist et al. 1995, "Ketoconazole in the management of paraneoplastic Cushing's syndrome secondary to ectopic adrenocorticotropin production." *J Clin Oncol* 13(1): 157-64). Ketoconazole also lowers blood pressure in the majority of patients with Cushing's syndrome (Sonino et al. 1991, supra; Fallo et al. (1993). "Response of hypertension to conventional antihypertensive treatment and/or steroidogenesis inhibitors in Cushing's syndrome." *J Intern Med* 234 (6): 595-8).

Pharmacological reduction in cortisol synthesis has also been evaluated in patients with type 2 diabetes. Metyrapone also inhibits 11β hydroxylase, the final step in the synthesis of cortisol and has been used in short-term studies to determine whether acute suppression of cortisol can have beneficial effects on glucose homeostasis. One study (Atiea et al. (1990). "Early morning hyperglycaemia "dawn phenomenon" in non-insulin dependent diabetes mellitus (NIDDM): effects of cortisol suppression by metyrapone." *Diabetes Res* 14(4): 181-5) used metyrapone to suppress the normal early morning rise in cortisol and reported that this intervention prevented the normal rise in glucose that occurs over this time period. One study suppressed endogenous cortisol synthesis in patients with type 1 diabetes using metyrapone and then infused cortisol to either mimic the normal nocturnal rise in cortisol or to produce a lower basal level of cortisol. In the patients with a "suppressed" cortisol profile, there was a significantly lower rate of glucose production (Dinneen et al. (1995). "Effects of the normal nocturnal rise in cortisol on carbohydrate and fat metabolism in IDDM." *Am J Physiol* 268(4 Pt 1): E595-603). Carbenoxolone inhibits the activity of both HSD1 and HSD2 and so lowers the exposure of liver and fat to cortisol. Another study treated both normal volunteers and patients with type 2 diabetes for 7 days with carbenoxolone (Andrews et al. (2003). "Effects of the 11 beta-hydroxysteroid dehydrogenase inhibitor carbenoxolone on insulin sensitivity in men with type 2 diabetes." *J Clin Endocrinol Metab* 88(1): 285-91). The patients with type 2 diabetes (but not the normal volunteers) demonstrated a decrease in glucose production rate during a euglycemic hyperinsulinemic hyperglucagonemic clamp. Racemic ketoconazole has also been tested in patients with type 2 diabetes. These trials are consistent with the conclusion that therapeutic use of this drug to suppress cortisol synthesis can have beneficial effects on glucose, blood pressure and cholesterol in patients with type 2 diabetes. While there may be an increase in cortisol levels or activity in patients with type 2 diabetes, therapeutic benefit can be obtained by a further reduction in cortisol levels or activity even in patients with normal cortisol levels or activity.

While therapeutic use of racemic ketoconazole in patients with type 2 diabetes has produced encouraging results, DIO-902 will be both more efficacious and safer. DIO-902 has a significantly lower $IC_{50}$ toward the key enzyme in cortisol synthesis (11β-hydroxylase) and a lower $IC_{50}$ toward a key enzyme in cholesterol synthesis (14α-lanosterol demethylase) than does the 2R,4S enantiomer (Rotstein et al. (1992). "Stereoisomers of ketoconazole: preparation and biological activity." *J Med Chem* 35(15): 2818-25), thus potentially allowing a lower dose of drug to achieve the same efficacy. As demonstrated in Example 1, in rats, DIO-902 is more potent with respect to reducing corticosterone and cholesterol than is the 2R,4S enantiomer.

Furthermore DIO-902 has a 12× higher $IC_{50}$ toward CYP7A ($IC_{50}$=2.4 microM) than does the 2R,4S enantiomer ($IC_{50}$=0.195 microM) (Rotstein et al. 1992, supra). Without intending to be bound by a particular mechanism, CYP7A suppression can lead to functional cholestasis and as a consequence there can be hepatic and plasma accumulation of potentially toxic metabolites such as oxystrols and bilirubin and xenobiotics such as ketoconazole itself. The reduced CYP7A inhibition associated with DIO-902 (compared to racemic ketoconazole) may account, at least in part, for the unchanged toxicokinetics of DIO-902 observed after repeated dosing.

Preclinical studies have associated glucocorticoid activity with insulin resistance, hyperglycemia and increased adiposity, and clinical studies support the rationale for using cortisol synthesis inhibitors such as ketoconazole as therapeutic options in patients with type 2 diabetes. Preclinical studies indicate that DIO-902 is safer and more efficacious than racemic ketoconazole.

C. Physical, Chemical, and Pharmaceutical Properties of an Illustrative Pharmaceutical Formulation of the Invention—DIO 902

DIO-902 is the single enantiomer 2S,4R ketoconazole and is derived from racemic ketoconazole. It is formulated using cellulose, lactose, cornstarch, colloidal silicon dioxide and magnesium stearate as an immediate release 200 mg strength tablet. The chemical name is 2S,4R cis-1-acetyl-4-[4-[[2-(2,4-dichlorophenyl)-2-(1H-imidazol-1-ylmethyl)-1,3-dioxolan-4-yl]methoxyl]phenyl]piperazine, the formula is $C_{26}H_{28}Cl_2N_4O_4$, and the molecular weight is 531.44. The CAS number is 65277-42-1, and the structural formula is provided below. The chiral centers are at the carbon atoms 2 and 4 as marked.

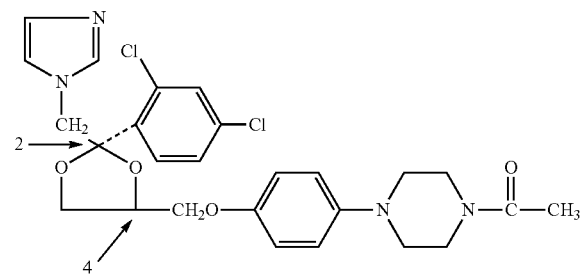

Ketoconazole is an imidazole-containing fungistatic compound. DIO-902 is an immediate release tablet to be taken orally and formulated as shown in the table below.

| Component | Percentage |
|---|---|
| 2S,4R ketoconazole; DIO-902 | 50% |
| Silicified Microcrystalline Cellulose, NF (Prosolv HD 90) | 16.5 |
| Lactose Monohydrate, NF (316 Fast Flo) | 22.4 |
| Corn Starch, NF (STA-Rx) | 10 |
| Colloidal Silicon Dioxide, NF (Cab-O-SilM5P) | 0.5 |
| Magesium Stearate, NF | 0.6 |

The drug product may be stored at room temperature and is anticipated to be stable for at least 2 years at 25° C. and 50% RH. The drug is packaged in blister packs.

D. Non-Clinical Studies

1. Overview of Nonclinical Studies

This section contains pharmacology and toxicology information for both DIO-902 and racemic ketoconazole. Pharmacology studies have included studies conducted to demonstrate the suppressive effects of DIO-902 on corticosterone synthesis, serum cholesterol and testosterone levels in rats. The antifungal activity of DIO-902 has also been investigated in an in vitro study. The toxicology studies with DIO-902 in dogs included a MTD study, a 7-day study, and a 28-day study (with toxicokinetics). Genotoxicity studies have also been conducted with DIO-902. Because DIO-902 is purified from racemic ketoconazole, the safety of the mixture is relevant to that of DIO-902. Thus, this section includes a summary of pharmacology and toxicology data taken primarily from the Summary Basis of Approval for NDA 18-533 for oral ketoconazole as well as data from the scientific literature and from a 28-day toxicity study in dogs.

2. Nonclinical Pharmacology

The primary pharmacological effect of DIO-902 will be through the suppression of cortisol synthesis. Pharmacological intervention to reduce plasma cortisol has proved effective in treating diabetes, hypertension, and dyslipidemia in patents with Cushing's syndrome (Sónino et al. 1991, supra; Winquist et al. 1995, supra). Preclinical studies have associated glucocorticoid activity with insulin resistance, hyperglycemia, and increased adiposity (for a review see (McMahon et al. 1988, supra). Secondary benefits of DIO-902 administration will include reduced cholesterol levels, reduced visceral adiposity, and reduced blood pressure.

A key enzymatic activity relevant to the therapeutic benefit of DIO-902 is 11β hydroxylase, an enzyme that catalyzes the ultimate step in adrenal synthesis of cortisol. DIO-902 has been shown to inhibit this enzyme with an $IC_{50}$ of 0.15 µM (see Table below). Because in rats the main glucocorticoid is corticosterone (in humans the main glucocorticoid is cortisol), the suppressive effects of DIO-902 on corticosterone synthesis was investigated in rats. In one study, male Sprague Dawley rats (10/group) received a single oral (via gastric tube) dose of 0, 50, 100, 200, 400, and 600 mg/kg of 2S,4R-ketoconazole (DIO-902), 2R,4S-ketoconazole, or racemic ketoconazole and were sacrificed 4 hours post later. In another study, male Sprague Dawley rats (10/group) received a single oral (via gastric tube) dose of 0 or 200 mg/kg of 2S,4R-ketoconazole (DIO-902), 2R,4S-ketoconazole, or the racemate and were sacrificed at 4, 8, 12, 16, 20, and 24 hours post dosing. The results indicated that DIO-902 (the 2S,4R enantiomer) reduces plasma corticosterone and does so more potently than the 2R,4S enantiomer, as shown in the following Tables. For more detail see Example 1.

Inhibition by DIO-902 of Enzymes that Catalyze Glucocorticol Synthesis

| Enzyme | $IC_{50}$ for ketoconazole | $IC_{50}$ for 2S,4R (DIO-902) | $IC_{50}$ for 2R,4S | Reference |
|---|---|---|---|---|
| 17α hydroxylase | 0.91 | NAV | NAV | (Ideyama et al. 1999*) |
| 17, 20 lyase | 0.017 | 0.05 | 2.38 | (Rotstein et al. 1992, supra; Ideyama et al. 1999) |
| 11β hydroxylase | NAV | 0.15 | 0.61 | (Rotstein et al. 1992) |
| aromatase | NAV | 110 | 39.6 | (Rotstein et al. 1992) |

All $IC_{50}$ values in the Table above are given in µM. While there may be a single enzyme or complex responsible for both the 17β hydroxylase and the 17,20 lyase activities, different $IC_{50}$ values have been reported for several inhibitors. NAV means data not available. * Ideyama et al. (1999). "YM116, 2-(1H-imidazol-4-ylmethyl)-9H-carbazole, decreases adrenal androgen synthesis by inhibiting C17-20 lyase activity in NCI-H295 human adrenocortical carcinoma cells." *Jpn J Pharmacol* 79(2): 213-20

In the following Table, the effect of ketoconazole enantiomers on corticosteroid levels in rats is reported. In the Table, corticosteroid levels (mean±SEM; ng/mL) were determined four hours after oral gavage of the indicated drug (N=10/group). There was a single control group (dosed with vehicle).

Effect of Ketoconazole Enantiomers on Corticosteroid Levels in Rats

| Dose | Corticosteroid Levels (mean ± SEM; ng/mL) | | |
|---|---|---|---|
| (mg/kg) | 2S,4R (DIO-902) | 2R,4S | Racemate |
| 0 | 320 ± 9.4 | 320 ± 9.4 | 320 ± 9.4 |
| 50 | 186 ± 14.9 | 226 ± 30.1 | 215 ± 20.7 |
| 100 | 139 ± 10.9 | 196 ± 17.2 | 210 ± 15.5 |
| 200 | 100 ± 8.6 | 217 ± 25.8 | 135 ± 13.7 |
| 400 | 84 ± 11.6 | 192 ± 11.6 | 113 ± 6.6 |
| 600 | 80 ± 7.8 | 167 ± 6.8 | 115 ± 14.3 |

The following Table presents the data from a study of the time course of corticosterone inhibition in rates following a single oral 200 mg/kg dose of ketoconazole enantiomers. Corticosterone levels (mean±SEM; ng/mL) were determined at the indicated times after oral gavage of the indicated drug at 200 mg/kg. So as to minimize the confounding effect of the diurnal corticosterone rhythm, all the rats were sacrificed at the same time of day (1800 hours) and the time of drug administration was determined to allow this (N=10/group). The means of the vehicle treated groups are used as the time zero control point.

Time Course of Corticosterone Inhibition in Rats Following a Single Oral 200 mg/kg Dose of Ketoconazole Enantiomers

| Time | Corticosteroid Levels (mean ± SEM; ng/mL) | | | |
|---|---|---|---|---|
| (hours) | Vehicle | 2S,4R (DIO-902) | 2R,4S | Racemate |
| 4 | 298 ± 15.8 | 98 ± 10 | 191 ± 14 | 134 ± 10 |
| 8 | 374 ± 17 | 116 ± 13 | 206 ± 13 | 163 ± 11 |
| 12 | 296 ± 21 | 113 ± 8 | 175 ± 9 | 153 ± 14 |
| 16 | 289 ± 16 | 133 ± 17 | 171 ± 9 | 132 ± 6 |
| 20 | 232 ± 26 | 136 ± 12 | 169 ± 7 | 147 ± 17 |
| 24 | 341 ± 24 | 103 ± 14 | 182 ± 10 | 151 ± 14 |

The secondary benefits of DIO-902 administration will include reduced LDL and total cholesterol, reduced visceral adiposity, reduced blood pressure, and antifungal activity. The mechanism of action for DIO-902 induced cholesterol suppression as well as pharmacology studies demonstrating the effects of DIO-902 on serum cholesterol and testosterone levels in the rat are discussed below.

Racemic ketoconazole may directly lower cholesterol through inhibition of lanosterol 14α demethylase activity, and the 2S,4R enantiomer has a two fold lower $IC_{50}$ for this enzyme than does the other enantiomer (Rotstein et al. 1992, supra). The cholesterol lowering activity of the 2S,4R enantiomer is expected to be further increased through diminished inhibition of CYP7A, the principal enzyme controlling cholesterol catabolism. Decreased CYP7A activity (in both humans (Pullinger et al. (2002). "Human cholesterol 7alpha-hydroxylase (CYP7A1) deficiency has a hypercholesterolemic phenotype." *J Clin Invest* 110(1): 109-17) and in mice (Erickson et al. (2003). "Hypercholesterolemia and changes in lipid and bile acid metabolism in male and female cyp7A1-deficient mice." *J Lipid Res* 44(5): 1001-9) can lead to hypercholesterolemia, and so the suppression of CYP7A by ketoconazole in humans (Pullinger et al. 2002, supra) is expected to attenuate the cholesterol lowering effect of this drug. The single enantiomer 2S,4R-ketoconazole is expected not to reduce CYP7A activity to the same extent as racemic ketoconazole. One study demonstrated that the $IC_{50}$ of 2S,4R-ketoconazole (DIO-902) towards CYP7A (as measured by cholesterol 7α-hydroxylase activity) is 2.4 µM and the $IC_{50}$ of 2R,4S-ketoconazole is 0.195 M, providing support that DIO-902 has a 12× greater $IC_{50}$ toward CYP7A than 2R,4S-ketoconazole (Rotstein et al. 1992, supra).

A study was conducted to demonstrate the effect of DIO-902 on cholesterol levels in rats. In this study, male Sprague Dawley rats (10/group) received a single oral (via gastric tube) dose of 0 or 200 mg/kg of 2S,4R-ketoconazole (DIO-902), 2R,4S-ketoconazole, or the racemate, and were sacrificed at 4, 8, 12, 16, 20, and 24 hours post dosing. The results, reported in the following Table, showed a small decrease in cholesterol levels at 16, 20 and 24 hours after treatment with the 2S,4R enantiomer but not with the racemate or with the other enantiomer. Cholesterol levels (mean±SEM; mg/dL) were determined at the indicated times after oral gavage of the indicated drug at 200 mg/kg. All rats were sacrificed at the same time of day (1800 hours) and the time of drug administration was determined appropriately (N=10/group).

Effect of Ketoconazole Enantiomers on Serum Cholesterol in Rats

| Time | Cholesterol levels (mean ± SEM; mg/dL) | | | |
|---|---|---|---|---|
| (hours) | Vehicle | 2S,4R (DIO-902) | 2R,4S | Racemate |
| 4 | 77.3 ± 3.9 | 69.6 ± 1.9 | 85.1 ± 7 | 81.2 ± 3.9 |
| 8 | 73.5 ± .5 | 73.5 ± 3.1 | 85.1 ± 5.4 | 73.5 ± 2.3 |
| 12 | 69.6 ± 3.5 | 77.3 ± 3.9 | 77.3 ± 1.9 | 69.6 ± 2.3 |
| 16 | 69.6 ± 1.9 | 61.9 ± 3.1 | 77.3 ± 4.6 | 69.6 ± 3.1 |
| 20 | 69.6 ± 1.9 | 58 ± 1.2 | 69.6 ± 2.7 | 65.7 ± 2.7 |
| 24 | 65.7 ± 2.7 | 61.9 ± 3.1 | 69.6 ± 1.5 | 65.7 ± 3.9 |

Two studies were conducted to investigate the effect of DIO-902 on testosterone levels in rats. In one study, male Sprague Dawley rats (10/group) received a single oral (via gastric tube) dose of 0, 50, 100, 200, 400, and 600 mg/kg of 2S,4R-ketoconazole (DIO-902), 2R,4S-ketoconazole, or racemic ketoconazole, and were sacrificed 4 hours post dosing. In another study, male Sprague Dawley rats (10/group) received a single oral (via gastric tube) dose of 0 or 200 mg/kg of 2S,4R-ketoconazole (DIO-902), 2R,4S-ketoconazole, or the racemate, and were sacrificed at 4, 8, 12, 16, 20, and 24 hours post dosing. The results shown in the following Tables demonstrate that the 2S,4R enantiomer (DIO-902) is more potent at suppressing testosterone than is the other enantiomer (2R,4S). For the results shown in the immediately following Table, testosterone levels (mean±SEM; nmol/L) were determined four hours after oral gavage of the indicated drug (N=10/group). There was a single control group (dosed with vehicle).

Effect of Ketoconazole Enantiomers on Testosterone in Rats

| Dose | Testosterone levels (mean ± SEM; nmol/L) | | |
|---|---|---|---|
| (mg/kg) | 2S,4R (DIO-902) | 2R,4S | Racemate |
| 0 | 2.7 ± 0.5 | 2.7 ± 0.5 | 2.7 ± 0.5 |
| 50 | 2.6 ± 0.7 | 2.5 ± 0.5 | 2.7 ± 0.6 |
| 100 | 0.8 ± 0.3 | 1.3 ± 0.2 | 1.7 ± 0.5 |
| 200 | 0.2 ± 0.1 | 1.4 ± 0.4 | 0.4 ± 0.2 |
| 400 | 0.3 ± 0.1 | 0.7 ± 0.2 | 0.4 ± 0.2 |
| 600 | 0 ± 0 | 1.6 ± 0.3 | 0.8 ± 0.1 |

For the results shown in the following Table, testosterone levels (mean±SEM; nmol/L) were determined at the indicated times after oral gavage of the indicated drug at 200 mg/kg. All rats were sacrificed at the same time of day (1800 hours), and the time of drug administration was determined appropriately (N=10/group). The means of the vehicle treated groups are used as the time zero control point. Although 2S,4R is more potent than 2R,4S with respect to acute suppression of testosterone, the overall physiological consequences may be reduced with 2S,4R as opposed to 2R,4S. As noted in Example 2, the concentration of the 2S,4R enantiomer does not increase with repeated doses. This is contrast to the concentration of the racemic mixture, which does increase with repeated doses. Thus, with repeated doses of the racemic mixture, testosterone suppression will become more marked with time. As also noted in Example 3, the concentration of the racemic mixture 24 hours after taking the drug increases markedly between the first and subsequent doses. Thus testosterone suppression will last progressively longer during the day in the inter-drug interval. As the 2S,4R enantiomer does not inhibit its own clearance, the period during the day when testosterone production is suppressed will not get progressively longer.

Time Course of Testosterone Suppression Following a Single Dose (200 mg/kg) of Ketoconazole Enantiomers in Rats

| Time | Testosterone levels (mean ± SEM; nmol/L) | | | |
|---|---|---|---|---|
| hours) | Vehicle | 2S,4R (DIO-902) | 2R,4S | Racemate |
| 4 | 3.7 ± 0.7 | 0.8 ± 0.2 | 3.4 ± 0.5 | 1.6 ± 0.6 |
| 8 | 8.9 ± 1.4 | 5.9 ± 0.8 | 8.6 ± 2.0 | 8.0 ± 1.0 |
| 12 | 5.4 ± 1.1 | 3.4 ± 0.5 | 5.6 ± 1.1 | 4.6 ± 0.6 |
| 16 | 5.6 ± 0.9 | 3.9 ± 0.6 | 5.5 ± 0.9 | 3.8 ± 0.5 |
| 20 | 5.7 ± 1.0 | 5.2 ± 0.6 | 5.2 ± 1.1 | 5.6 ± 0.8 |
| 24 | 5.5 ± 0.9 | 4.4 ± 0.7 | 6.0 ± 1.0 | 5.9 ± 0.5 |

3. Antifungal Activity

In an in vitro study, both DIO-902 and 2R,4S-ketoconazole exhibit antifungal activity as reported in the following Table. In this study, yeast isolates were incubated with racemic ketoconazole, DIO-902 (2S,4R-ketoconazole), 2R,4S-ketoconazole, or solvent (DMSO) for 48 hours at 36±1° C., and the minimum inhibitory concentration (MIC) was determined. The MIC was defined as the lowest concentration that substantially inhibited growth of the organism (i.e. that caused a prominent decrease of greater than or equal to 80% in turbidity compared to that of controls).

Antifungal Activity of DIO-902

| DSM Strain | | MIC (mg/L) | | |
|---|---|---|---|---|
| Number | Organism | Ketoconazole | 2R,4S | 2S,4R (DIO-902) |
| 11948 | *Candida albicans* | <0.015 | <0.015 | <0.015 |
| 11944 | *Candida albicans* | <0.015 | <0.015 | <0.015 |
| 11949 | *Candida albicans* | 0.125 | 0.25 | 0.125 |
| 11945 | *Candida albicans* | 0.03 | 0.03 | 0.03 |
| 11943 | *Candida albicans* | <0.015 | <0.015 | <0.015 |
| 11225 | *Candida albicans* | <0.015 | <0.015 | <0.015 |
| 98-St-00799 | *Candida albicans* | <0.015 | <0.015 | <0.015 |
| 11950 | *Candida glabrata* | 0.25 | 0.25 | 0.25 |
| 11226 | *Candida glabrata* | 0.5 | 0.5 | 0.5 |
| 11947 | *Candida guilliermondii* | 0.125 | 0.25 | 0.06 |
| 11954 | *Candida kefyr* | 0.03 | 0.03 | 0.03 |
| 05784 | *Candida parapsilosis* | 0.03 | 0.06 | 0.03 |
| 11224 | *Candida parapsilosis* | <0.015 | 0.06 | 0.03 |
| 11952 | *Candida tropicalis* | 4 | 4 | 2 |
| 11953 | *Candida tropicalis* | 0.06 | 0.125 | 0.06 |
| 11951 | *Candida tropicalis* | 0.125 | 0.125 | 0.06 |
| 11960 | *Cryptococcus neoformans* | 0.125 | 0.125 | 0.125 |
| 11959 | *Cryptococcus neoformans* | 0.06 | 0.03 | 0.03 |
| 11956 | *Issachenkia orientalis* | 0.25 | 0.5 | 0.25 |
| 11958 | *Issachenkia orientalis* | 1 | 2 | 1 |
| 01333 | *Saccharomyces cervisiae* | 0.25 | 0.25 | 0.25 |

While the anti-fungal activity of the 2S,4R enantiomer has been asserted without proof, these results demonstrate for the first time that this enantiomer is surprisingly more effective as an anti-fungal agent than the racemate and/or 2R,4S enantiomer against a variety of fungi, including *Issatchenkia orientalis, Issachenkla orientalis, Cryptococcus neoformans, Candida tropicalis, Candida parapsilosis, Candida guilliermondii*, and *Candida albicans*, or certain strains thereof. In one embodiment, the present invention provides a method for treating a fungal infection of one of these fungi or strains of fungi by administering a therapeutically effective amount of a pharmaceutical composition of the 2S,4R enantiomer of ketoconazole substantially free of the 2R,4S enantiomer.

4. Safety Pharmacology

The inhibitory potential of DIO-902 on CYP3A inhibitory activity has been studied. In this study, DIO-902 and the 2R,4S ketoconazole enantiomer were shown to have $IC_{50}$ values that were comparable to each other and to the racemic mixture although there was be a small (2×) increase in the $IC_{50}$ of the 2S,4R-enantiomer toward CYP3A5. DIO-902 (0.005-50 µM for CYP3A4 and 0.01-100 µM for CYP3A5) was added to microsomes prepared from human liver or to recombinant 3A4 and 3A5. As a positive control and as a comparator, the activities of the other enantiomer (2R,4S) and the racemic mixture were also determined. The substrate used in these experiments was quinone, an established substrate for the CYP3A4 and CYP3A5 (Mirghani et al. (2002). "Enzyme kinetics for the formation of 3-hydroxyquinine and three new metabolites of quinine in vitro; 3-hydroxylation by CYP3A4 is indeed the major metabolic pathway." *Drug Metab Diapos* 30(12): 1368-71).

Activity of DIO-902 Towards the Hydroxylation of Quinine

|  | HLM pool Quinine 160 µM $IC_{50}$ µM | rCYP3A4 Quinine 30 µM $IC_{50}$ µM | rCYP3A5 Quinine 20 µM $IC_{50}$ µM |
|---|---|---|---|
| racemate | 0.27 | 0.12 | 0.38 |
| 2R, 4S | 0.37 | 0.14 | 0.40 |
| 2S, 4R (DIO-902) | 0.29 | 0.19 | 0.71 |

HLM: human liver microsomes

The scientific literature reports the inhibitory activity of the 2S,4R enantiomer on Cytochome P450 Inhibition. One study (Rotstein et al. 1992, supra) evaluated the inhibitory activity of the two ketoconazole enantiomers (2S,4R and 2R,4S ketoconazole) toward the hydroxylation of progesterone, lauric acid, and cholesterol which are markers for various P450 enzymes. The $IC_{50}$ of the 2S,4R enantiomer was slightly greater than that of 2R,4S. The $IC_{50}$ for the inhibition of CYP3A4 (via 6β-hydroxylase) was similar to that of racemic ketoconazole as reported by Swinney, 1990. Specifically, the $IC_{50}$ for the inhibition of progesterone 6µ-hydroxylase metabolism in rat hepatic microsomes was 1.4 µM. Due to the similar $IC_{50}$ for CYP450 3A4 inhibition for the 2S,4R enantiomer and racemic ketoconazole, the potential for drug metabolism interactions for these two compounds is expected to be similar. However as noted below and in Example 2, the potential for DIO-902 to cause a change in PK profile of an administered drug through an inhibition of drug excretion is significantly reduced compared to that of the other enantiomer.

In regards to activity of the P450 enzyme, CYP7A (cholesterol 7α hydroxylase), the results, shown in the Table below, demonstrate that the $IC_{50}$ of the 2S,4R enantiomer is approximately 12-fold higher than the $IC_{50}$ of the 2R,4S enantiomer. CYP7A is relevant to the issue of drug interaction, because this enzyme controls bile formation, and thus, the exposure to drugs that are normally cleared via the bile may be altered under conditions of reduced bile formation and flow. It has been shown that racemic ketoconazole inhibits bile formation through inhibition of CYP7A. Racemic ketoconazole has been shown to reduce bile flow and the clearance of endogenous metabolites (cholesterol) and xenobiotics (bromosulphopthalein) into the bile (Princen et al. (1986). "Ketoconazole blocks bile acid synthesis in hepatocyte monolayer cultures and in vivo in rat by inhibiting cholesterol 7 alpha-hydroxylase." *J Clin Invest* 78(4): 1064-71; Gaeta and Tripodi (1987). "Ketoconazole impairs biliary excretory function in the isolated perfused rat liver." *Naunyn Schmiedebergs Arch Pharmacol* 335(6): 697-700). That the 2S,4R enantiomer has a reduced impact on the pharmacokinetics of a drug (ketoconazole) that is normally cleared via the bile may due to the observation that the $IC_{50}$ of the 2S,4R enantiomer is approximately 12-fold higher than the $IC_{50}$ of the 2R,4S enantiomer toward CYP7A. As a consequence of this reduced inhibition of drug clearance, the 2S,4R anantiomer will significantly decrease the risk of hepatic damage as compared to the other enantiomer or to the racemic mixture of the two enantiomers that constitute ketoconazole.

P450 Inhibitory Activity of the Ketoconazole Enantiomers (Rotstein et al. 1992, Supra)

|  |  |  | $IC_{50}$ (µM) | |
|---|---|---|---|---|
| Substrate | Reaction | Associated P450 | 2S,4R (DIO-902) | 2R,4S |
| Progesterone | 2α hydroxylase | 2C11 | 104 | 84 |
| Progesterone | 6β hydroxylase | 3A | 1.3 | 0.79 |
| Progesterone | 16α hydroxylase | 2B1, 2B2, 1A1, 2C11, 3A | 84 | 69 |
| Progesterone | 21 hydoxylase | 2C6 | 9.0 | 11.2 |
| Lauric acid | hydroxylase | 4A | >100 | <100 |
| Cholesterol | 7α hydroxylase | 7A | 2.4 | 0.195 |

5. Nonclinical Pharmacokinetics

The absorption of DIO-902 (2S,4R enantiomer) was studied during a 28 day dog toxicology study. In this study, dogs were treated orally with DIO-902 doses of 2, 6.5, and 20 mg/kg. Serum samples were taken after the $1^{st}$ and $28^{th}$ daily dose of the 2S,4R enantiomer. For comparison, a group of dogs were to receive racemic ketoconazole at a dose of 40 mg/kg/day for 28 days. This dose was administered as planned for the first 9 days of the study; however, due to toxicity, the 40 mg/kg dose was discontinued after the 9' day, and animals in this group were left untreated for the next 5 days (days 10 to 14). Beginning on study day 15 and continuing through study day 28, animals were treated with 20 mg/kg of ketoconazole. Toxicokinetic parameters are summarized in the Tables below.

The plasma levels in the dogs dosed with DIO-902 at 2 mg/kg/day were below detection for most of the 24 hour profile. Thus, an accurate AUC could not be calculated for this dose. Where AUC was calculated, it was based on the values that were above the limit of detection over the time period from 0 to 12 hours post dosing (see Table below). As such, the AUC from the 2 mg/kg dose cannot reliably be compared with that of the other dose levels. The AUC and $C_{max}$ values at 2, 6.5, and 20 mg/kg were comparable between Day 1 and Day 28 for each DIO-902 dose level, indicating minimal to no accumulation with repeat dosing. No sex differences were seen in DIO-902 treated animals. $C_{max}$ and AUC levels in animals treated with 2 mg/kg or 6.5 mg/kg DIO-902 were approximately proportional to dose. At the 6.5 and 20 mg/kg dose levels, the increase in AUC and $C_{max}$ levels were increased more than that of the increase in dose. $T_{max}$ values ranged from 1 to 8 hours on Day 1 and 1 to 12 hours on Day 28 (see the second of the two following Tables).

For racemic ketoconazole, the AUC and plasma drug levels on Day 28 were notably lower than that seen on Day 1 due to the interruption in dosing and the reduced dose levels administered. However, both the AUC and $C_{max}$ values are decreased more than the decrease in dose from Day 1 to Day 28. Thus, Day 1 and Day 28 data for racemic ketoconazole cannot be reliably compared. When comparing the Day 1 data for the ketoconazole 40 mg/kg dose with that of the 20 mg/kg dose for DIO-902, the AUC and $C_{max}$ values in the animals treated with racemic ketoconazole are approximately double that of the animals treated with 20 mg/kg of DIO-902. On Day 28, the AUC and $C_{max}$ values from the animals treated with 20 mg/kg of racemic ketoconazole were substantially lower than that of animals treated with 20 mg/kg of DIO-902.

Due to the issues discussed above with the doses of racemic ketoconazole, for comparison purposes, additional data for racemic ketoconazole from another 28-day toxicity study in dogs was obtained. In this study, dogs (3/sex/group) were treated with oral doses of 2.5, 10, or 40 mg/kg of racemic ketoconazole in a powder suspension or 2.5, 10 or 40 mg/kg of racemic ketoconazole in an oil suspension once daily for 28 days. Toxicokinetic samples were collected on Day 1 and during Weeks 2 and 4. For comparison with the current data, Day 1 and Day 28 data are presented from the administered ketoconazole powder suspension (10 and 40 mg/kg). Data from the oil suspension was similar to the powder suspension. The $C_{max}$ values for DIO-902 on day 28 for dogs dosed at 20 mg/kg/day were between 9.94 microg/ml and 9.95 microg/ml (see the second of the two following Tables). For comparison, a dose of 10 mg/kg of racemic ketoconazole produced a $C_{max}$ of 7.52 to 9.20 μg/ml (on day 28) and a dose of 40 mg/kg led to a $C_{max}$ of 42.78 to 46.75 μg/ml (on day 28). In contrast to that seen with racemic ketoconazole, it is apparent that the AUC and $C_{max}$ for 2S,4R ketoconazole (DIO-902) were not significantly different on day 28 as compared to day 1. A significant increase between day 1 and day 28 was noted for racemic ketoconazole (see the second of the two following Tables). For the following Table: *Days of treatment. The limit of detection was 0.25 μg/mL a: Data for racemic ketoconazole. b: Data for racemic ketoconazole. Values represent mean of 3 animals.

Plasma Drug Levels of DIO-902 and Racemic Ketoconazole in Dogs Following Single and Repeat Oral Dosing

| Drug | Dose (mg/kg) | Day* | Sex | Drug concentration (μg/ml) at the indicated time (hours) | | | | | |
|---|---|---|---|---|---|---|---|---|---|
| | | | | 0 | 1 | 2 | 4 | 8 | 12 |
| DIO-902 | 2 | 1 | M | <0.25 | 0.40 | 0.45 | <0.25 | <0.25 | <0.25 |
| | | | F | <0.25 | <0.25 | 0.27 | 0.28 | <0.25 | <0.25 |
| | 2 | 28 | M | <0.25 | 0.66 | 0.54 | 0.38 | <0.25 | <0.25 |
| | | | F | <0.25 | 0.29 | 0.52 | 0.30 | <0.25 | <0.25 |
| | 6.5 | 1 | M | <0.25 | 1.19 | 1.62 | 1.25 | 0.41 | 0.40 |
| | | | F | <0.25 | <0.25 | 0.44 | 2.32 | 0.50 | <0.25 |
| | 6.5 | 28 | M | <0.25 | 1.17 | 1.39 | 1.54 | 1.33 | 0.88 |
| | | | F | <0.25 | 0.25 | 1.25 | 1.85 | 1.27 | 0.34 |
| | 20 | 1 | M | <0.25 | 7.05 | 8.30 | 6.15 | 2.92 | 6.74 |
| | | | F | <0.25 | <0.25 | 0.65 | 9.72 | 9.95 | 5.44 |
| | 20 | 28 | M | 1.19 | 9.13 | 9.78 | 8.17 | 5.86 | 4.25 |
| | | | F | 2.88 | 1.78 | 2.43 | 6.42 | 9.83 | 6.53 |
| Racemic ketoconazole[a] | 20 | 28 | M | <0.25 | <0.25 | 0.28 | <0.25 | <0.25 | <0.25 |
| | | | F | <0.25 | <0.25 | 0.27 | 0.35 | 0.31 | <0.25 |
| | 40 | 1 | M | <0.25 | 5.60 | 8.87 | 10.82 | 16.63 | 12.76 |
| | | | F | <0.25 | 4.29 | 12.33 | 20.09 | 18.33 | 14.82 |
| Racemic ketoconazole[b] | 10 | 1 | M | <0.25 | 0.38 | 0.62 | 1.18 | 0.33 | <0.25 |
| | | | F | <0.25 | 1.30 | 1.23 | 0.59 | <0.25 | <0.25 |
| | 10 | 28 | M | <0.25 | 7.53 | 8.63 | 6.20 | 1.44 | 0.43 |
| | | | F | <0.25 | 7.28 | 7.21 | 4.39 | 0.85 | <0.25 |
| | 40 | 1 | M | <0.25 | 10.30 | 14.60 | 23.09 | 10.12 | 6.70 |
| | | | F | <0.25 | 5.65 | 5.76 | 3.30 | 1.84 | 1.55 |
| | 40 | 28 | M | 3.97 | 11.90 | 24.63 | 32.72 | 46.75 | 28.29 |
| | | | F | 12.84 | 12.28 | 31.55 | 38.59 | 40.45 | 29.91 |

Toxicokinetics of DIO-902 in Dogs Following Single and Repeat Oral Dosing

| Drug | Dose (mg/kg) | Days of treatment | Sex | $AUC_{(0-12)}$ (μg·h/mL) | Cmax (μg/mL) | Tmax Range (hour) |
|---|---|---|---|---|---|---|
| DIO-902 | 2 | 1 | M | 2.39* | 0.51 | 1-2 |
| | | | F | 2.57* | 0.45 | 2-4 |
| | 2 | 28 | M | 3.26 | 0.68 | 1-4 |
| | | | F | 2.76* | 0.75 | 1-8 |
| | 6.5 | 1 | M | 12.23** | 2.00 | 1-4 |
| | | | F | 4.70* | 2.57 | 2-4 |
| | 6.5 | 28 | M | 14.65 | 2.01 | 1-8 |
| | | | F | 12.86 | 2.41 | 2-8 |
| | 20 | 1 | M | 60.59 | 9.38 | 1-4 |
| | | | F | 80.63** | 14.66 | 4-8 |
| | 20 | 28 | M | 80.00 | 9.94 | 2-4 |
| | | | F | 77.85 | 9.95 | 8-12 |
| Racemic ketoconazole[a] | 40 | 1 | M | 142.80 | 16.63 | 8 |
| | | | F | 185.41 | 21.28 | 4-8 |
| | 20 | 28 | M | 3.42* | 0.51 | 1-8 |
| | | | F | 4.70* | 0.55 | 2-8 |

-continued

| Drug | Dose (mg/kg) | Days of treatment | Sex | $AUC_{(0-12)}$ (µg · h/mL) | Cmax (µg/mL) | Tmax Range (hour) |
|---|---|---|---|---|---|---|
| Racemic ketoconazole[b] | 10 | 1 | M | 9.01 | 1.43 | 2-4 |
| | | | F | 6.73 | 1.58 | 1-8 |
| | 10 | 28 | M | 44.15 | 9.20 | 1-2 |
| | | | F | 33.11 | 7.52 | 1-2 |
| | 40 | 1 | M | 179.82 | 23.32 | 2-4 |
| | | | F | 42.94 | 6.23 | 2-12 |
| | | | M | 542.28 | 46.75 | 8 |
| | | | F | 639.19 | 42.78 | 4-8 |

For the preceding Table, the data provided in the first of the two preceding Tables were used to derive AUC and Cmax values on the first day of dosing and again after 28 daily days of dosing. Values represent mean of 3 animals. *n=1, **n=2. a: Data for racemic ketoconazole. b: Data for racemic ketoconazole. AUC data is for 0-24 h.

6. Repeat Dose Toxicity of DIO-902

The toxicity of DIO-902 has been investigated in dogs in a maximum tolerated dose study, a 7-day study, and a 28-day study in dogs. The MTD investigation and 7-day study were conducted as separate phases of a single study.

In a GLP maximum tolerated dose study, Beagle dogs (2/sex) were treated orally (capsule) with ascending doses (20, 40, 60 and 80 mg/kg) of the 2S,4R enantiomer. As a control, a separate set of 2 male and 2 female dogs was treated with vehicle. Animals were treated with each dose for three days before ascending to the next higher dose. There were no deaths during the ascending phase. Clinical signs were noted at 40 mg/kg (vomiting). At higher doses head shaking, tremors, salivation, colored urine and liquid feces were noted. The 80 mg/kg dose was abandoned on welfare grounds. Food intake and weight gain was reduced at all doses.

After the end of the MTD study, the 4 animals that were treated with vehicle were treated orally (capsule) with 40 mg/kg of the enantiomer for 7 days. No control group was included. All animals survived to scheduled sacrifice. During the fixed dose (7 days at 40 mg/kg/day), one dog was noted as being thin, and one dog was noted as having tears. There were no post-dosing observations. Food consumption by all four animals was reduced and all four lost weight over the seven day study period. Hematological analysis suggested a decrease in reticulocytes (absolute and relative) in one dog and a 20% reduction in total white cell numbers. The mean ALT levels in the treated dogs increased by less than two fold compared to the mean determined prior to dosing. There was no significant change in any of the other liver enzymes measures. Macroscopic findings at necropsy were limited to areas of GI irritation. There may have been an increase in the weights of liver and kidney, but in the absence of a concurrent control, this could not be concluded with confidence.

In a 28 day GLP study, beagle dogs (3/sex/group) received daily oral 2S,4R enantiomer doses of doses of 0 (placebo), 2, 6.5, or 20 mg/kg. A separate control group (3/sex) was included and treated orally with racemic ketoconazole at an initial dose of 40 mg/kg/day. At 40 mg/kg of racemic ketoconazole, significant body weight losses (up to 17.3%) led to cessation of dosing after 9 days. The dogs in this group (3/sex) were taken off drug for 6 days and then restarted at 20 mg/kg/day. The toxicokinetic profile taken at 28 days indicated that the $C_{max}$ of racemic ketoconazole on day 28 was less than 5% of that determined on day 1. Thus, for data comparison, this group cannot be used with confidence as a comparator. Unless otherwise noted below, all further references to drugs and doses in this study will refer to the single enantiomer 2S,4R.

Toxicokinetic data indicated that DIO-902 was systemically absorbed. At a 2 mg/kg DIO-902 dose level, the plasma drug levels were below the limit of detection at many of the timepoints between 1 and 12 hours post dosing. Thus, AUC was calculated using data from timepoints were plasma drug levels were above the limit of detection. For each dose, no sex differences were observed and no accumulation occurred over the 28 days of dosing.

The dogs dosed with DIO-902 at 20 mg/kg/day ate approximately 25-35% less food than those in the placebo control group. The dogs dosed at 20 mg/kg/day gained 0.25 kg (males) and 0.14 kg (females) compared to the placebo treated dogs that gained 1.1 kg (males) and 0.9 kg (females) in body weight. The trends indicate that most of the effects on body weight were in the first two weeks of the study and that at the end of the study the dogs dosed at 20 mg/kg/day were gaining weight at a rate similar to the placebo control group. Food intake also increased in the 20 mg/kg/day group although still below the placebo control group. At the intermediate doses there were no obvious effects on food intake or weight gain.

There were no measurable effects of DIO-902 at these doses on any of the opthalmological or electrocardiographic parameters that were measured. Specifically in the dogs treated with DIO-902 at 20 mg/kg/day, there was no obvious QTc prolongation. There were no hematological changes noted. There was no change in the urinalysis. The only change in any serum chemistry measures was a reduction in cholesterol. There were trends of decrease in the kidney weights in the female dogs and trends of an increase in the relative (but not absolute) weights of the liver and adrenals in male and females. There were no remarkable microscopic findings at any dose.

7. Other Toxicity Testing

No reproductive toxicology studies have been conducted with DIO-902; however, the reproductive toxicity of racemic ketoconazole has been extensively investigated studied.

DIO-902 was found to be negative for genotoxicity in an Ames assay and in the mouse lymphoma assay. In the Ames assay, DIO-902 was assayed with respect to mutation induction in five different histidine requiring strains of *Salmonella typhimurium*. Exposure to the DIO-902 produced no dose related and repeatable increase in revertant numbers. In the lymphoma assay, DIO-902 (with and without S-9 activation) was studied with respect to the induction of mutations at the thymidine kinase locus in mouse L5178Y lymphoma cells. DIO-902 did not reproducibly or meaningfully induce mutation at the TK locus in three independent experiments in the absence of S-9 and two independent experiments in the presence of S-9 when tested up to toxic doses.

Carcinogenicity studies have not been conducted with DIO-902. Racemic ketoconazole has been found to be non-carcinogenic (SBA for NDA 18-533).

Administration of the 2S,4R enantiomer substantially free of the 2R,4S enantiomer is expected to reduce the risk of hepatic reactions sometimes seen following administration of racemic ketoconazole (Stricker et al. (1986). "Ketoconazole-associated hepatic injury. A clinicopathological study of 55 cases." *J Hepatol* 3(3): 399-406; Lake-Bakaar et al. (1987). "Hepatic reactions associated with ketoconazole in the United Kingdom." *Br Med J (Clin Res Ed)* 294(6569): 419-22; Van Cauteren et al. (1990). "Safety aspects of oral antifungal agents." *Br J Clin Pract Suppl* 71: 47-9; and Rodriguez and Acosta (1997). "Metabolism of ketoconazole and deacetylated ketoconazole by rat hepatic microsomes and flavin-containing monooxygenases." *Drug Metab Dispos* 25(6): 772-7). Ketoconazole induced hepatic reactions are usually described as idiosyncratic (Stricker et al. 1986, supra) implying that the underlying mechanism(s) are not known. It has been demonstrated that racemic ketoconazole inhibits bile formation in rats through inhibition of CYP7A (Princen et al. 1986, supra). Racemic ketoconazole has been shown to inhibit human CYP7A (Rotstein et al. 1992, supra), reduce bile acid synthesis by human hepatocytes (Princen et al. 1986, supra), and inhibit bile acid production (Miettinen 1988, supra) in treated patients. We believe that a key component of ketoconazole induced hepatotoxicity is the inhibition of CYP7A. Because DIO-902 has a 12× higher $IC_{50}$ toward CYP7A ($IC_{50}$=2.4 µM) than does the other enantiomer 2R,4S ($IC_{50}$-0.195 µM) and does not undergo the time dependent increase in drug concentration seen for the racemate, DIO-902 will be associated with a significantly lower incidence of liver reactions. The two effects should be interactive; that is, the racemate will accumulate more than DIO-902, and the higher drug accumulation of the racemate will lead to an even greater relative inhibitory effect on CYP7A than is implied from the cell free assays. The relevant drug concentrations attained in humans, the relative levels in plasma of the two enantiomers, and the relative $IC_{50}$ values are consistent with this expectation.

E. Pharmacokinetics of DIO-902 in Humans

No clinical trials have yet been conducted with DIO-902. However the pharmacokinetic profile of the individual enantiomers following the first and the fifth 200 mg dose of racemic ketoconazole (doses given every twelve hours) have been presented in poster form (Gerber (2003). "Stereoselective pharmacokinetics (PK) of oral ketoconazole (K) in healthy subjects." ACAAF poster). The pharmacokinetic data are summarized in the following Table. The exposure to DIO-902, 2S,4R enantiomer, is approximately 2.5 fold that of the 2R,4S enantiomer. It is not clear if this results from a difference in bioavailability or clearance. After five doses, the AUC and the Cmax increase for both enantiomers. As exposure to the 2R,4S enantiomer could alter the clearance of both 2S,4R and 2R,4S enantiomers, this result is not necessarily at variance with the pharmacokinetic data obtained from preclinical results obtained in dogs dosed with DIO-902, the single enantiomer. Pharmacokinetic Data (Gerber 2003, supra)

|  | Following first dose | | Following fifth dose | |
| --- | --- | --- | --- | --- |
|  | DIO-902; 2S,4R | 2R,4S | DIO-902; 2S,4R | 2R,4S |
| AUC 0-12 (µg*min/mL) | 302 +/− 38 | 820 +/− 142 | 538 +/− 74 | 1543 +/− 231 |
| T½ (minutes) | 133 +/− 14 | 97 +/− 8 | 217 +/− 30 | 158 +/− 19 |
| $C_{max}$ µg/mL | 1.06 +/− 0.13 | 3.4 +/− 0.44 | 1.53 +/− 0.19 | 4.77 +/− 0.55 |

F. Idiosyncratic Liver Reactions in Humans

The idiosyncratic liver reactions to racemic ketoconazole have been described (Stricker et al. 1986, supra). The description of these responses as being idiosyncratic implies that there is no clear understanding of the mechanism(s). Any coherent mechanistic explanation should encompass the asymptomatic increase in liver enzymes that occurs within a short period of time in 1-10% of treated patients following first exposure, as well as the relatively infrequent incidence of more severe responses. There is no consistent evidence linking ketoconazole to immune mediated mechanisms.

Although no relationship between dose and hepatotoxicity in humans has been described, there is a clear correlation between AUC and liver damage in rabbits (Ma et al. (2003). "Hepatotoxicity and toxicokinetics of ketoconazole in rabbits." *Acta Pharmacol Sin* 24(8): 778-82). These authors reported that, in rabbits, 40 mg/kg ketoconazole induced morphological changes in hepatocytes and an increase in serum liver enzymes. This dose is comparable to the highest dose tested in a one year dog study. Acute in vitro hepatoxicity was studied by others (Rodriguez and Acosta 1997, supra, and Rodriguez and Acosta (1997). "N-deacetyl ketoconazole-induced hepatotoxicity in a primary culture system of rat hepatocytes." *Toxicology* 117(2-3): 123-31). In these studies, rat hepatocytes were cultured in the presence of increasing doses of ketoconazole (up to 200 microM) for times that ranged from 0.5 hour to 4 hours. These authors found that there was both a dose and time component to the release of lactate dehydrogenase (LDH). At the longest time exposure studied (four hours), there was no detectable effect of ketoconazole at concentrations below 75 microM (39 µg/mL). There is also a suggestion from preclinical animal models that the metabolites of ketoconazole (specifically deacetylated ketoconazole (DAK)) is a more potent mitochondrial inhibitor than ketoconazole (Rodriquez and Acosta (1996). "Inhibition of mitochondrial function in isolated rat liver mitochondria by azole antifungals." *J Biochem Toxicol* 11(3): 127-31). The in vitro $IC_{50}$ for DAK inhibition of succinate dehydrogenase is 350 microM (in comparison to the $C_{max}$ of unmetabolized ketoconazole of 12.3 microM following a 400 mg dose in humans (Huang et al. (1986). "Pharmacokinetics and dose proportionality of ketoconazole in normal volunteers." *Antimicrob Agents Chemother* 30(2): 206-1.0) It is possible that these and related direct effects of ketoconazole (and the metabolites) could lead to an idiosyncratic reaction if there were patients that were significantly more susceptible than the general population.

Material provided here and in Example 2 indicate that a key component of ketoconazole induced hepatotoxicity is the inhibition of CYP7A. Because DIO-902 has a 12× higher $IC_{50}$ toward CYP7A ($IC_{50}$=2.4 microM) than does the other enantiomer 2R,4S ($IC_{50}$=0.195 microM) (Rotstein et al. 1992, supra) and does not undergo the time dependent increase in drug concentration seen for the racemate, DIO-902 will be associated with a significantly lower incidence of liver reactions. As noted above, the two effects will be interactive; that is the racemate will accumulate more than DIO-902 and the higher drug accumulation of the racemate will lead to an even greater relative inhibitory effect on CYP7A than is implied from the cell free assays. The inhibition of CYP7A by racemic ketoconazole may cause a hepatic reaction indirectly through reduced bile acid synthesis and the consequent reduction in bile flow and increase in potentially toxic metabolites. Ketoconazole may further exacerbate this process by directly increasing the level of potentially hepatotoxic oxysterols.

Racemic ketoconazole inhibits bile formation in rats through inhibition of CYP7A (Princen et al. 1986, supra)

(bile synthesis is blocked when cholesterol is used as a substrate but not when 7α-cholesterol is used as a substrate). The inhibition of bile acid synthesis by ketoconazole is a direct effect on hepatocytes (Whiting et al. (1989). "Bile acid synthesis and secretion by rabbit hepatocytes in primary monolayer culture: comparison with rat hepatocytes." *Biochim Biophys Acta* 1001(2): 176-84). Bile flow is also reduced by ketoconazole and the clearance of endogenous metabolites (cholesterol) (Princen et al. 1986, supra) and xenobiotics ((bromosulphopthalein (Gaeta and Tripodi 1987, supra)) into the bile is reduced. As ketoconazole is excreted into the bile, it would be anticipated that ketoconazole might inhibit its own clearance and lead to increased plasma concentrations. This increase in drug concentration has been noted in humans and in dogs. That CYP7A inhibition causes functional cholestasis (reduced bile acid synthesis and bile flow) is consistent with the recognition that CYP7A is the rate limiting step in bile acid synthesis, and bile acid synthesis appears to be rate limiting for bile flow. In humans, the genetic absence of functional CYP7A causes a profound decrease in focal bile acids (Pullinger et al. 2002, supra) and in mice, the genetic absence of CYP7A can cause cholestasis (Arnon et al. (1998). "Cholesterol 7-hydroxylase knockout mouse: a model for monohydroxy bile acid-related neonatal cholestasis," *Gastroenterology* 115(5): 1223-8).

The relationship between CYP7A inhibition, cholestasis, and liver damage is also consistent with other rodent models that do not use ketoconazole as an experimental tool. Thus, ethinylestradiol induced cholestasis in rats correlates with a suppression of bile flow, liver bile acid content, and liver cholesterol content. Epomediol prevents ethinylestradiol induced cholestasis and produces significant (albeit small) reversals in these three measures. CYP7A activity was suppressed by ethinylestradiol and returned to normal with epomediol (Cuevas et al. (2001). "Effect of epomediol on ethinyloestradiol-induced changes in bile acid and cholesterol metabolism in rats." *Clin Exp Pharmacol Physiol* 28(8): 637-42). Ketoconazole inhibits human microsomal CYP7A, reduces bile acid synthesis by human hepatocytes (Princen et al. 1986, supra) and inhibits bile acid production (Miettinen 1988, supra) in treated patients. Functional cholestasis can cause subsequent hepatic damage through reduced clearance of endogenous metabolites such as oxysterols (below) and bilirubin and by reduced clearance of exogenous metabolites such as ketoconazole.

In addition to the wider ranging impact of ketoconazole mediated inhibition of CYP7A noted above there may be a more specific effect through decreased clearance of oxysterols. Oxysterols (hydroxylated sterols) are formed as precursors to cholesterol or via subsequent hydroxylation of cholesterol. They are removed from the liver via conversion to bile acids or solubilized in the bile. The most abundant human enzyme able to initiate the conversion of oxysterols to bile acids is CYP7A (Norlin et al. (2000). "Oxysterol 7 alpha-hydroxylase activity by cholesterol 7 alpha-hydroxylase (CYP7A)." *J Biol Chem* 275(44): 34046-53), and, as noted above, ketoconazole can inhibit this enzyme as well as increase the levels of some oxysterols (Miettinen 1988, supra). If the conversion fails or bile flow falls, oxysterols can accumulate and liver damage may occur. Oxysterols are cytotoxic to a variety of cell types including hepatoma cell lines (Hietter et al. (1984). "Antagonist action of cholesterol towards the toxicity of hydroxysterols on cultured hepatoma cells." *Biochem Biophys Res Commun* 120(2): 657-64; Leighton et al. (1991). "Activation of the silent endogenous cholesterol-7-alpha-hydroxylase gene in rat hepatoma cells: a new complementation group having resistance to 25-hydroxycholesterol." *Mol Cell Biol* 11(4): 2049-56; O'Callaghan et al. 1999). "Oxysterol-induced cell death in U937 and HepG2 cells at reduced and normal serum concentrations." *Eur J Nutr* 38(6): 255-62). More specifically, one study has reported that H35 rat hepatoma cells die in the presence of the oxysterol 25-hydroxy cholesterol and that resistance to 25-hydroxy cholesterol can be brought about by the expression of human CYP7. Ketoconazole abrogates this CYP7 mediated resistance (Leighton et al. 1991, supra).

The magnitude of the decrease in bile acid synthesis and the increase in oxysterols following ketoconazole mediated CYP7A inhibition will depend on the level of CYP7B (oxysterol 7alpha hydroxylase). As CYP7B is under genetic and physiological control (Ran et al. (2003). "Regulation of oxysterol 7alpha-hydroxylase (CYP7B1) in the rat." *Metabolism* 52(5): 636-42; Jakobsson et al. (2004). "A functional C-G polymorphism in the CYP7B1 promoter region and its different distribution in Orientals and Caucasians." *Pharmacogenomics J* 4(4): 245-50), it is likely that there will be a spectrum of activities in a human population, and it could be expected that, in some proportion of ketoconazole treated patients, the level of CYP7B will be insufficient to compensate for the ketoconazole mediated suppression of CYP7A. It is known that insufficient CYP7B can cause liver damage if CYP7A activity is significantly reduced. At the extreme end of this insufficiency, a complete lack of CYP7B can be fatal. Thus, one study reported on the fatal liver damage that developed in an infant lacking a functional copy of CYP7B. The liver damage was suggested to occur as a direct toxic effect as well as from inhibition of the formation of bile acids and, possibly, from an induction of oxidant stress. The accumulating oxysterols could not be further metabolized by CYP7A because this enzyme is not expressed in infants (Setchell et al. (1998). "Identification of a new inborn error in bile acid synthesis: mutation of the oxysterol 7alpha-hydroxylase gene causes severe neonatal liver disease." *J Clin Invest* 102(9): 1690-703).

The observations made in human patients treated with ketoconazole require an explanation for why only a subset of patients develops a transient mild increase in serum liver enzymes and an even smaller subset develop a more severe reaction. It is possible that, on first exposure to ketoconazole, CYP7A is inhibited, bile formation and flow is reduced, and oxysterols and other potentially toxic metabolites begin to accumulate. In the majority of patients, CYP7B is expressed at sufficient levels or is induced rapidly enough that liver damage is not detectable. It has been demonstrated that in the complete absence of CYP7A the alternate pathway for bile acid synthesis is upregulated (Pullinger et al. 2002, supra). In this model, in approximately 1%-10% of individuals, CYP7B is expressed at lower levels and/or the induction of CYP7B is delayed and, as a consequence, minor liver damage occurs. However CYP7B would then be upregulated, damage is limited and resolves even in the continued exposure to ketoconazole. In a smaller number of patients, the induction of CYP7B may be insufficient to compensate for the inhibition of CYP7A, and more serious liver damage occurs. In particularly susceptible patients, ketoconazole mediated CYP7A inhibition could lead to ketoconazole accumulation and drug concentrations that are high enough to initiate direct toxicities.

It is important to note that despite ketoconazole being an important, commercially available anti-fungal drug and that the hepatic reactions caused by ketoconazole can be life threatening, there are no reports in the literature of any evidence that directly links ketoconazole to hepatic reactions through an inhibition of CYP7A, and there are no reports in the literature that suggest the 2S,4R enantiomer would be a safer drug based on the lower $IC_{50}$ of this enantiomer toward CYP7A. U.S. Pat. No. 6,040,307 describes a method for determining whether a drug could induce hepatotoxicity that utilizes hepatic microsomes derived from frozen tissue. However, hepatotoxicity can only be measured using intact live hepatocytes, preferably in a live animal.

The material provided here and in Example 3 provide an internally consistent mechanism for the hepatic reactions caused by racemic ketoconazole. Because DIO-902 has a 12 fold lower $IC_{50}$ toward CYP7A than does the 2R,4S enantiomer, patients treated with DIO-902 will have a significantly lower incidence of hepatic reactions. The relevant drug concentrations attained in humans, the relative levels in plasma of the two enantiomers, and the relative $IC_{50}$ values are consistent with this possibility. The pharmacokinetic profile for the two enantiomers following five BID doses of 200 mg of the racemate has been obtained. For the 2R,4S enantiomer, the $IC_{50}$ toward CYP7A is 0.195 microM, and if the intrahepatic concentration of the drug is approximately 20% of the total plasma drug concentration (Venkatakrishnan er al. (2000). "Effects of the antifungal agents on oxidative drug metabolism: clinical relevance." *Clin Pharmacokinet* 38(2): 111-80), then the enantiomer will have to reach a total plasma concentration of approximately 1 microM (approximately 0.5 microg/mL) to inhibit effectively intrahepatic CYP7A. This is within the concentrations of this enantiomer following dosing with 200 mg of the racemate. In contrast, DIO-902 has an $IC_{50}$ of 2.4 microM. Thus, assuming similar drug availability, the total plasma concentration required for DIO-902 to inhibit CYP7A significantly would be 12 microM (approximately 6.3 microg/mL). Even with the significantly greater exposure for DIO-902, the $C_{max}$ of this enantiomer is only 65% of this level, and thus, CYP7A is unlikely to be inhibited by DIO-902 at these doses.

G. Clinical Study of DIO-902

A Phase 1 trial in patients with type 2 diabetes mellitus can be conducted to investigate the safety and tolerability of DIO-902. A synopsis of such a trial is provided below. Such a trial would be the first human clinical study of the 2S,4R enantiomer of ketoconazole administered substantially free of the 2R, 4S enantiomer. The primary objective is to evaluate the safety and tolerability of 14 daily doses of the 2S,4R enantiomer in subjects with type 2 diabetes. The secondary objectives are to determine the pharmacokinetic (PK) profile in plasma of the 2S,4R enantiomer after a single dosing and after fourteen daily doses. In addition the pharmacodynamic activity of fourteen daily doses of the 2S,4R enantiomer, as reflected by changes in blood pressure, cholesterol, plasma and salivary cortisol, cortisol binding globulin, measures of glycemic control (fructosamine, continuous glucose monitoring, insulin levels, and fasting blood glucose) and plasma free fatty acids are measured.

Seven (7) dose groups are studied. Six subjects are enrolled into each dose group. The dose groups are as follows:

Ketoconazole 400 mg po QD
2S,4R enantiomer 200 mg po QD
2S,4R enantiomer 400 mg po QD
2S,4R enantiomer 600 mg po QD
2S,4R enantiomer 800 mg po QD
2S,4R enantiomer 400 mg po BID
Placebo po QD The dose of ketoconazole is based on the recommended maximum dose in the product label for use in fungal infections. Dose levels of the 2S,4R enantiomer to be studied are based on the knowledge that 50% of racemic ketoconazole is the enantiomer 2S,4R, extensive clinical experience with racemic ketoconazole at doses significantly higher than those recommended in the drug label, toxicokinetic profiles of racemic ketoconazole and the 2S,4R enantiomer in dogs, and a 28 day toxicology study of the 2S,4R enantiomer in dogs. The 2S,4R enantiomer and racemic ketoconazole are supplied as 200 mg tablets for oral administration. Placebo tablets matching both the 2S,4R enantiomer tablets and the racemic ketoconazole tablets are also supplied.

The invention, having been described in detail and exemplified above, has a wide variety of embodiments; consequently, while certain embodiments of the invention have been described herein in detail, numerous alternative embodiments are contemplated as falling within the scope of the following claims.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same.

What is claimed is:

1. A method for treating Cushing's Syndrome in a patient in need of such treatment, said method comprising administering a therapeutically effective amount of 2S,4R ketoconazole enantiomer substantially free of the 2R,4S ketoconazole enantiomer to said patient.

2. The method of claim 1, wherein the therapeutically effective amount of the 2S,4R ketoconazole enantiomer is from about 50 mg to about 600 mg.

* * * * *

UNITED STATES PATENT AND TRADEMARK OFFICE

(12)                 CERTIFICATE EXTENDING PATENT TERM
UNDER 35 U.S.C. 156

(68) PATENT NO. : 9,918,984

(45) ISSUED : March 20, 2018

(75) INVENTOR : Per MARIN

(73) PATENT OWNER : Xeris Pharmaceuticals, Inc.

(95) PRODUCT : RECORLEV® (levoketoconazole)

This is to certify that an application under 35 U.S.C. 156 has been filed in the United States Patent and Trademark Office, requesting extension of the term of U.S. Patent No. 9,918,984 based upon the regulatory review of the product RECORLEV® (levoketoconazole) by the Food and Drug Administration. According to United States Patent and Trademark Office records, the original expiration date of the patent as of the date of issuance of this certificate is January 10, 2026. Because it appears that the requirements of the law have been met, this certificate extends the term of the patent for the period of

(94)                         844 days subject to the payment of maintenance fees as provided by law, with all rights pertaining thereto as provided by 35 U.S.C. 156.

I have caused the seal of the United States Patent and Trademark Office to be affixed this 15th day of December 2025.

John A. Squires
Under Secretary of Commerce for Intellectual Property and
Director of the United States Patent and Trademark Office